US010496793B1

(12) United States Patent
Lawrence et al.

(10) Patent No.: US 10,496,793 B1
(45) Date of Patent: Dec. 3, 2019

(54) SYSTEMS AND METHODS FOR DETERMINING ELIGIBILITY IN A PRESCRIPTION SAFETY NETWORK PROGRAM

(71) Applicant: McKesson Corporation, San Francisco, CA (US)

(72) Inventors: Douglas Lawrence, Fountain Hills, AZ (US); Marlin G. Kester, Jr., Downingtown, PA (US); Patricia A. daCosta, Atlanta, GA (US)

(73) Assignee: MCKESSON CORPORATION, San Francisco, CA (US)

( * ) Notice: Subject to any disclaimer, the term of this patent is extended or adjusted under 35 U.S.C. 154(b) by 898 days.

(21) Appl. No.: 14/669,658

(22) Filed: Mar. 26, 2015

Related U.S. Application Data

(60) Provisional application No. 62/091,663, filed on Dec. 15, 2014.

(51) Int. Cl.
*G06F 19/00* (2018.01)
*G06Q 50/22* (2018.01)

(52) U.S. Cl.
CPC ......... *G06F 19/3456* (2013.01); *G06Q 50/22* (2013.01)

(58) Field of Classification Search
None
See application file for complete search history.

(56) References Cited

U.S. PATENT DOCUMENTS

| 5,628,530 A | 5/1997 | Thornton |
| 5,970,472 A | 10/1999 | Allsop et al. |
| 6,012,035 A | 1/2000 | Freeman et al. |
| 6,045,501 A | 4/2000 | Elsayed et al. |

(Continued)

FOREIGN PATENT DOCUMENTS

| CA | 2482370 A1 | 3/2006 |
| WO | 1995003569 A3 | 2/1995 |

(Continued)

OTHER PUBLICATIONS https://www.fda.gov/downloads/ForIndustry/UserFees/PrescriptionDrugUserFee/UCM361087.htm, The TIRF REMS Access Program: Chain Pharmacy Enrollment Form, Jul. 1, 2013, FDA, pp. 1-3 (Year: 2013).*

(Continued)

*Primary Examiner* — Devin C Hein
(74) *Attorney, Agent, or Firm* — Ballard Spahr LLP

(57) ABSTRACT

Systems and methods are provided for determining eligibility in a prescription safety network program, such as a risk evaluation and mitigation strategies (REMS) program. Enrollment information can be received from a prescriber of medication, such as a doctor, to enroll in a prescription safety network program. The prescriber enrollment information can be stored in a first database and the prescriber can be provided the ability to enroll patients in the prescription safety network program in a second database that is separate and distinct from the first database. Patient enrollment data for the prescription safety network program can be received from the prescriber and stored in the second database. Further, pharmacy/pharmacist enrollment data for the prescription safety network program can be received from a pharmacy/pharmacist and stored in the second database.

18 Claims, 7 Drawing Sheets

(56) References Cited

U.S. PATENT DOCUMENTS

| | | | |
|---|---|---|---|
| 6,055,507 A | 4/2000 | Cunningham | |
| 6,208,973 B1 | 3/2001 | Boyer et al. | |
| 6,315,720 B1 | 11/2001 | Williams et al. | |
| 6,561,976 B2 | 5/2003 | Elsayed et al. | |
| 6,561,977 B2 | 5/2003 | Williams et al. | |
| 6,602,469 B1 | 8/2003 | Maus et al. | |
| 6,757,898 B1 | 6/2004 | Ilsen et al. | |
| 6,769,228 B1 | 8/2004 | Mahar | |
| 6,952,681 B2 | 10/2005 | McQuade et al. | |
| 6,994,249 B2 | 2/2006 | Peterka et al. | |
| 7,040,856 B2 | 5/2006 | Reich | |
| 7,086,133 B2 | 8/2006 | Reich | |
| 7,096,072 B2 | 8/2006 | Engleson et al. | |
| 7,103,419 B2 | 9/2006 | Engleson et al. | |
| 7,107,106 B2 | 9/2006 | Engleson et al. | |
| 7,117,041 B2 | 10/2006 | Engleson et al. | |
| 7,155,397 B2 | 12/2006 | Alexander et al. | |
| 7,171,277 B2 | 1/2007 | Engleson et al. | |
| 7,175,081 B2 | 2/2007 | Andreasson et al. | |
| 7,469,213 B1 | 12/2008 | Rao | |
| 7,483,756 B2 | 1/2009 | Engleson et al. | |
| 7,668,730 B2 | 2/2010 | Reardan et al. | |
| 7,739,127 B1 | 6/2010 | Hall | |
| 7,765,106 B2 | 7/2010 | Reardan et al. | |
| 7,765,107 B2 | 7/2010 | Reardan et al. | |
| 7,813,938 B2 | 10/2010 | Kusterbeck | |
| 7,885,824 B1 | 2/2011 | Koneru | |
| 7,895,059 B2 | 2/2011 | Reardan et al. | |
| 7,976,508 B2 | 7/2011 | Hoag | |
| 8,036,911 B2 | 10/2011 | Bellon et al. | |
| 8,112,290 B2 | 2/2012 | Maurer et al. | |
| 8,150,709 B2 | 4/2012 | Miller et al. | |
| 8,265,959 B2 | 9/2012 | McKenzie et al. | |
| 8,386,274 B1 | 2/2013 | Pinsonneault | |
| 8,392,219 B1 | 3/2013 | Pinsonneault | |
| 2002/0002495 A1 | 1/2002 | Ullman | |
| 2002/0087583 A1 | 7/2002 | Morgan et al. | |
| 2002/0111828 A1 | 8/2002 | Bloder et al. | |
| 2002/0111832 A1 | 8/2002 | Judge | |
| 2002/0198831 A1 | 12/2002 | Patricelli et al. | |
| 2003/0009367 A1 | 1/2003 | Morrison | |
| 2003/0050731 A1 | 3/2003 | Rosenblum | |
| 2003/0050799 A1 | 3/2003 | Jay et al. | |
| 2003/0055683 A1 | 3/2003 | Gibson et al. | |
| 2003/0093295 A1 | 5/2003 | Lilly et al. | |
| 2003/0130875 A1 | 7/2003 | Hawash et al. | |
| 2003/0144884 A1 | 7/2003 | Mayaud | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0019794 A1 | 1/2004 | Moradi et al. | |
| 2004/0039599 A1 | 2/2004 | Fralic | |
| 2004/0073457 A1 | 4/2004 | Kalies | |
| 2004/0078234 A1 | 4/2004 | Tallal, Jr. | |
| 2004/0117323 A1 | 6/2004 | Mindala | |
| 2004/0148198 A1 | 7/2004 | Kalies | |
| 2004/0249745 A1 | 12/2004 | Baaren | |
| 2005/0015280 A1 | 1/2005 | Gabel et al. | |
| 2005/0060201 A1 | 3/2005 | Connely, III et al. | |
| 2005/0102169 A1 | 5/2005 | Wilson | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240473 A1 | 10/2005 | Ayers, Jr. et al. | |
| 2005/0240523 A1 | 10/2005 | Richardson et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0054682 A1 | 3/2006 | de la Huerga | |
| 2006/0136263 A1 | 6/2006 | Fry et al. | |
| 2006/0149784 A1 | 7/2006 | Tholl et al. | |
| 2006/0184391 A1 | 8/2006 | Barre et al. | |
| 2006/0259363 A1 | 11/2006 | Jhetam et al. | |
| 2006/0271405 A1 | 11/2006 | Cipolle et al. | |
| 2007/0005402 A1 | 1/2007 | Kennedy et al. | |
| 2007/0043586 A1 | 2/2007 | Arellano | |
| 2007/0050209 A1 | 3/2007 | Yered | |
| 2007/0088461 A1 | 4/2007 | Haitin et al. | |
| 2007/0136100 A1 | 6/2007 | Daugherty et al. | |
| 2007/0214014 A1 | 9/2007 | Suwalski et al. | |
| 2007/0219825 A1 | 9/2007 | Maetzold et al. | |
| 2007/0226149 A1 | 9/2007 | McFarlin et al. | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2007/0260491 A1 | 11/2007 | Palmer et al. | |
| 2008/0076971 A1 | 3/2008 | Clapp | |
| 2008/0126135 A1 | 5/2008 | Woo | |
| 2008/0201173 A1 | 8/2008 | Takehara et al. | |
| 2008/0208626 A1 | 8/2008 | Greenman | |
| 2008/0306796 A1 | 12/2008 | Zimmerman et al. | |
| 2009/0012818 A1 | 1/2009 | Rodgers | |
| 2009/0094051 A1 | 4/2009 | Ard et al. | |
| 2009/0125324 A1 | 5/2009 | Keravich et al. | |
| 2009/0125326 A1 | 5/2009 | Wasson et al. | |
| 2009/0192819 A1 | 7/2009 | Zimmermann | |
| 2009/0246265 A1 | 10/2009 | Stinchcomb et al. | |
| 2010/0057489 A1 | 3/2010 | Howe et al. | |
| 2010/0082458 A1 | 4/2010 | Godlewski | |
| 2010/0256984 A1 | 10/2010 | Gold et al. | |
| 2010/0287002 A1 | 11/2010 | Barre et al. | |
| 2011/0010328 A1 | 1/2011 | Patel et al. | |
| 2011/0029327 A1 | 2/2011 | Dunlop | |
| 2011/0106556 A1 | 5/2011 | Patel et al. | |
| 2011/0119085 A1 | 5/2011 | Reardan et al. | |
| 2011/0145018 A1 | 6/2011 | Fotsch et al. | |
| 2011/0182807 A1 | 7/2011 | Fuisz et al. | |
| 2011/0184747 A1 | 7/2011 | Bozic et al. | |
| 2011/0184753 A1 | 7/2011 | Tripoli | |
| 2011/0184755 A1 | 7/2011 | Yamaga et al. | |
| 2011/0184756 A1 | 7/2011 | Yamaga et al. | |
| 2011/0209065 A1 | 8/2011 | Del Rio et al. | |
| 2013/0191139 A1* | 7/2013 | Chen | G06F 19/3456 705/2 |
| 2013/0339044 A1* | 12/2013 | Sheehan | G06Q 10/0635 705/2 |
| 2016/0292385 A1 | 10/2016 | Lekander et al. | |

FOREIGN PATENT DOCUMENTS

| | | | |
|---|---|---|---|
| WO | 2000039737 A1 | 7/2000 | |
| WO | 2007025295 A2 | 3/2007 | |

OTHER PUBLICATIONS

Non-Final Office Action for U.S. Appl. No. 13/789,855 dated Feb. 24, 2017.

Non-final Office Action for U.S. Appl. No. 13/461,731 dated Dec. 17, 2015.

Final Office Action for U.S. Appl. No. 12/552,825 dated Feb. 1, 2016.

Final Office Action for U.S. Appl. No. 13/461,731 dated Jun. 9, 2016.

Final Office Action for U.S. Appl. No. 13/789,855 dated Jun. 29, 2016.

Sampson, R.J., Taking Control of Health Care Costs, Best's Review—Life Health Insurance Edition, Nov. 1983, vol. 84, Issue 7, USA; Abstract only.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

(56) References Cited

OTHER PUBLICATIONS

Anonymous, Medic; On-line Goes In-House, Chain Store Age Executive, Jan. 1987, vol. 63, Issue 1, USA; Abstract only.
Anonymous, TechRx Announces Successful Beta Deployment of T-Rex. PR Newswire. May 13, 2002.
Federal Register—vol. 77, No. 39; Tuesday, Feb. 28, 2012; Notices (pp. 12059-12062).
"Many Pharmacists Now Administer Vaccinations;" Author Patti Neighmond; http://www.npr.org/templates/story/story.php?storyId=15380907; Published Oct. 18, 2007; Accessed Nov. 23, 2011.
Non-Final Office Action for U.S. Appl. No. 12/212,129 dated Apr. 18, 2011.
Non-Final Office Action for U.S. Appl. No. 12/468,102 dated May 27, 2011.
Final Office Action for U.S. Appl. No. 12/212,129 dated Aug. 18, 2011.
Final Office Action for U.S. Appl. No. 12/468,102 dated Nov. 16, 2011.
Non-Final Office Action for U.S. Appl. No. 12/212,129 dated Nov. 30, 2011.
Non-Final Office Action for U.S. Appl. No. 12/552,825 dated Dec. 2, 2011.
Non-Final Office Action for U.S. Appl. No. 12/776,974 dated Jan. 3, 2012.
Final Office Action for U.S. Appl. No. 12/212,129 dated Mar. 28, 2012.
Final Office Action for U.S. Appl. No. 12/552,825 dated May 1, 2012.
Final Office Action for U.S. Appl. No. 12/776,974 dated May 25, 2012.
Notice of Allowance for U.S. Appl. No. 12/776,974 dated Nov. 29, 2012.
Notice of Allowance for U.S. Appl. No. 12/212,129 dated Dec. 31, 2012.
Final Office Action for U.S. Appl. No. 12/468,102 dated Jan. 14, 2013.
Non-Final Office Action for U.S. Appl. No. 12/468,102 dated Sep. 5, 2013.
Non-Final Office Action for U.S. Appl. No. 13/461,731 dated Sep. 11, 2013.
Final Office Action for U.S. Appl. No. 12/468,102 dated Jan. 22, 2014.
Final Office Action for U.S. Appl. No. 13/461,731 dated Feb. 10, 2014.
Non-Final Office Action for U.S. Appl. No. 12/552,825 dated Aug. 12, 2014.
Non-Final Office Action for U.S. Appl. No. 12/468,102 dated Sep. 17, 2014.
Non-Final Office Action for U.S. Appl. No. 13/461,731 dated Dec. 4, 2014.
Non-Final Office Action for U.S. Appl. No. 13/789,855 dated Jan. 15, 2015.
Final Office Action for U.S. Appl. No. 12/468,102 dated Mar. 11, 2015.
Final Office Action for U.S. Appl. No. 13/461,731 dated May 6, 2015.
Non-final Office Action for U.S. Appl. No. 12/552,825 dated May 22, 2015.
Final Office Action for U.S. Appl. No. 13/789,855 dated Jul. 17, 2015.
Non-final Office Action for U.S. Appl. No. 12/468,102 dated Sep. 9, 2015.
Non-final Office Action for U.S. Appl. No. 13/789,855 dated Nov. 13, 2015.

* cited by examiner

SYSTEMS AND METHODS FOR DETERMINING ELIGIBILITY IN A PRESCRIPTION SAFETY NETWORK PROGRAM

CROSS-REFERENCE TO RELATED APPLICATIONS

This application claims priority under 35 U.S.C. § 119(e) to U.S. Provisional Patent Application No. 62/091,663, tiled Systems and Methods for Determining Eligibility in a Prescription Safety Network Program, which was filed on Dec. 15, 2014, the entire contents of which are hereby incorporated herein by reference for all purposes.

TECHNICAL FIELD

Aspects of the disclosure relate generally to the evaluation of electronic healthcare transactions, and more particularly, to systems and methods for determining if a patient is eligible to receive a medication or product that is part of a prescription safety network program and identified in an electronic healthcare transaction.

BACKGROUND

Highly regulated medications or products, such as those distributed under a prescription safety network program, may carry significant risks to patients. Examples of a prescription safety network program include Risk Evaluation & Mitigation Strategies (REMS). Properly educating not only the patient, but also the prescriber and the pharmacy/pharmacist dispensing the medication is necessary to reduce the risk to patients. As such, patients, prescribers, and pharmacies/pharmacists may be asked to enroll in the prescriber safety network program and satisfy the requirements of the prescription safety network program prior to receiving, prescribing, or dispensing the medications or products under the program. When a patient is prescribed a medication, it may be necessary to verify that one or more of the patient, pharmacy/pharmacist, and prescriber are enrolled in the prescription safety network program covering the medication or product prior to dispensing the medication or product to the patient.

BRIEF DESCRIPTION OF THE DRAWINGS

Reference will now be made to the accompanying drawings, which are not necessarily drawn to scale, and wherein.

DETAILED DESCRIPTION OF EXAMPLE EMBODIMENTS

Figure 1:
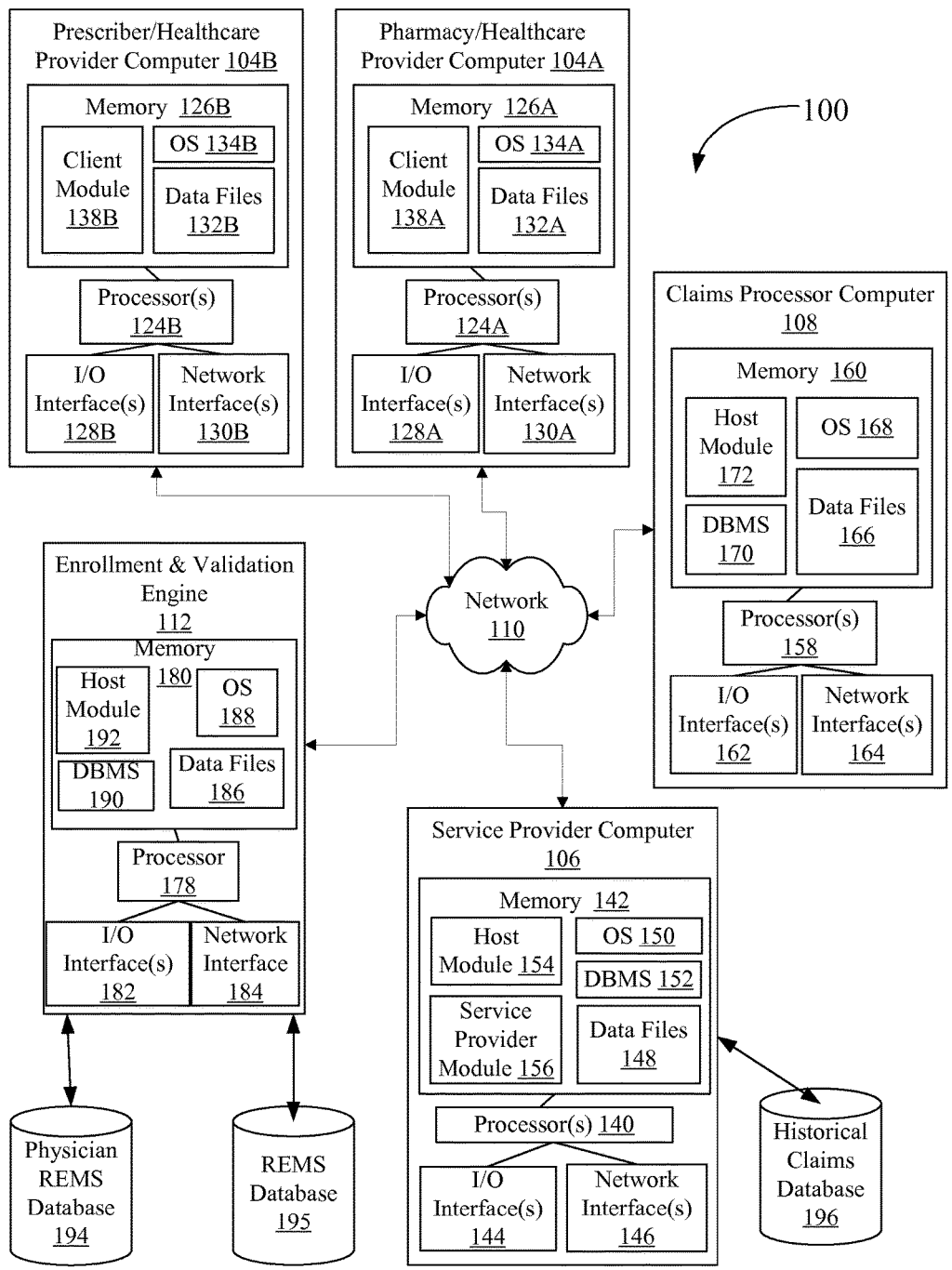
FIG. 1 illustrates an example overview of a system that facilitates determining eligibility in a prescription safety network program, according to one exemplary embodiment of the disclosure.

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods that facilitate enrollment in a prescription safety network program for a product or medication prescribed to a patient and determining a patient's eligibility to receive a medication/product that is in a prescription safety network program, as part of the processing of the healthcare transaction in real-time or near real-time. In certain example embodiments, the medication/product may be one that is potentially sensitive or may pose a greater than normal risk to a patient who is prescribed the medication or product. Examples of these sensitive, higher risk products include, but are not limited to, clozapine, acutaine, isotretinoin, and xyrem. For example, the medication clozapine requires that white blood cell (WBC) and absolute neutrophil count (ANC) be monitored at least monthly while a patient is taking clozapine. As another example, for a patient to take or continue taking the drug isotretinoin the patient may have to undergo monthly pregnancy testing. A Prescription Safety Network program may be utilized by a pharmaceutical manufacturer as part of a Risk Minimization Action Plan (RiskMAP) or Risk Evaluation and Mitigation Strategy (REMS) in accordance with U.S. Food and Drug Administration (FDA) guidelines. The registered or enrolled physicians or other healthcare providers, pharmacies/pharmacists, and/or patients/caregivers may receive educational or training information regarding one or more drugs or other products (e.g., medical devices), including medication safety guidelines or usage information. The registration or enrollment information may be stored for subsequent use in determining whether to provide authorization for filling or refilling a prescription.

For example, a physician or other prescriber (e.g., nurse, nurse practitioner, physician's assistant, physician's representative, hospital, doctor's office, or any other person legally permitted to prescribe a medication (hereinafter referred to generally as a "prescriber")) can enroll in a prescription safety network program for a particular product or medication. As part of the enrollment, the prescriber may provide certain identification and correspondence details, such as the prescriber's Drug Enforcement Administration (DEA) number, his/her office address, and desired method of communication (e.g., email address, phone number, etc.).

The prescriber may be provided with program and educational materials related to the medication/product. These materials may be provided to the prescriber electronically via a prescriber computer, faxed to the prescriber, or mailed to the prescriber. The prescriber may confirm that they have reviewed the materials and may agree to educate and enroll new patients in the prescription safety network program when those patients will be receiving the medication/product covered by the prescription safety network program. Upon enrollment and confirmation or review of the materials, the prescriber's enrollment information may be stored in a physician REMS database 194 and the prescriber may be provided log-in access to a prescription safety network program database (REMS database 195) via a network or portal (e.g., a website) of via another form of intermediary (e.g., an interactive voice recognition (IVR system) or call center operation). In certain example embodiments, there is no cross-linking of data between the physician REMS database 194 and the REMS database 195. Log-in access may take the form of a username and password or any other known log-in protocol. Log-in access may be provided to the prescriber for the purpose of enrolling patients into the REMS database 195 for the particular prescription safety network program when the patient will be prescribed a medication/product covered under the prescription safety network program. In an alternate embodiment (not shown) instead of a single REMS database 195 for storing enrollment information for all prescription safety network programs, multiple databases may be provided, each associated with a single prescription safety network program. In this alternate embodiment, physicians may only be provided log-in access to a particular prescription safety network program database upon enrolling and satisfying the requirements for that particular program. Providing separate databases for the enrollment information of each prescription safety network program can reduce the potential for errors as to whether a particular patient, pharmacy, and/or wholesale distributor is enrolled in a particular program. The patient identifying information entered into the REMS database 195 by the prescriber may be evaluated in a review of a healthcare transaction to determine if the patient is enrolled in the prescription safety network program for the particular medication/product.

Similarly, pharmacies/pharmacists and wholesale distributors of medications/products under a prescription safety network program may enroll in the prescription safety network program. For example, a pharmacist may enter into an agreement to participate in a prescription safety network program for a medication/product. The pharmacist may be provided program and educational materials related to the medication/product and may confirm review of those materials. The pharmacist may also agree to educate any patient receiving the medication/product in the prescription safety network program on the use and risks of the medication/product. Further, the pharmacist may agree to not resell the medication/product to another retail entity. The pharmacist may provide identifying information for the pharmacist/pharmacy, such as the pharmacist's name, DEA number, address, telephone number, and other contact information. All or a portion of the enrolled pharmacist's identifying information may be stored in the REMS database 195 and may be evaluated in a review of a healthcare transaction to determine if the pharmacist/pharmacy is enrolled in the prescription safety network program for the particular medication/product. In certain alternative embodiments, the identifying information for the enrolled pharmacy may be stored in a database separate from the patient identifying information under the prescription safety network program. Further, similar to the prescriber, in certain alternative embodiments, the pharmacist/pharmacy may be provided log-in access for the purpose of enrolling patients into the REMS database 195 for the particular prescription safety network program when the patient is prescribed a medication/product covered under the particular prescription safety network program.

Wholesale distributors may also enroll in the prescription safety network program. As part of the enrollment, the wholesale distributor may provide identifying information for the wholesale distributor. Further, the wholesale distributor may agree to verify that a pharmacy/pharmacist is enrolled in a prescription safety network program before sending medication/product covered under that program to the pharmacy. The wholesale distributor may also agree to not sell or otherwise transfer a medication/product covered under a prescription safety network program to another wholesaler or distributor. The identifying information for the wholesale distributor may be stored in the REMS database 195. In certain alternative embodiments, the identifying information for the enrolled wholesale distributor may be stored in a database separate from information for enrolled patients and/or pharmacists/pharmacies under the prescription safety network program.

When a patient receives a prescription for a medication/product covered under a prescription safety network program, the patient may take the prescription to a pharmacy. The pharmacist may generate and electronically transmit, via a pharmacy computer, a healthcare transaction, such as a predetermination of benefits transaction, prescription claim transaction, prescription claim or billing request, healthcare order transaction, or e-prescription transaction (e.g., electronic prescription order transaction, e-script, or e-prescription) for the patient to a service provider computer to determine if the patient is authorized to receive the medication/product. The healthcare transaction may include a medication/product identifier (e.g., a National Drug Code (NDC code) or RxNorm code), a prescriber identifier (e.g., DEA number), a pharmacy identifier (e.g., NPI code), and a patient identifier.

The service provider computer may provide the healthcare transaction to an enrollment and validation engine to determine if the patient is eligible to receive the prescribed medication. As part of that review, the medication/product identifier in the healthcare transaction may be compared to a schedule of medication/product identifiers for medications/products that are under the requirements of a prescription safety network program. If the medication/product is part of a prescription safety network program, one or more patient identifiers in the healthcare transaction may be compared to enrolled patient information in the REMS database 195 to determine if a match exists. If a match exists, the patient will be considered enrolled in the prescription safety network program. Furthermore, since the prescriber is the person who enrolls the patient in the prescription safety network program, the prescriber identified in the healthcare transaction may also be considered enrolled without actually searching the physician REMS database 194. If no match exists, the patient will be considered not enrolled and a notification may be generated and transmitted back to the pharmacy computer from which the healthcare transaction originated.

If the patient is enrolled, the pharmacy identifier in the healthcare transaction may be compared to enrolled pharmacist/pharmacy information in the REMS database 195 to determine if a match exists. If no match exists, the pharmacy will be considered not enrolled in the prescription safety network program and a notification of denial may be generated and transmitted back to the pharmacy computer. If a match does exist, a notification of authorization may be generated and transmitted back to the pharmacy computer.

In certain example embodiments, prior to the notification of authorization being generated and transmitted, another comparison may be made. For example, in certain embodiments, the REMS database 195 may also include prescriber identifiers (e.g., DEA numbers) for prescribers that are no longer enrolled in (or deactivated from) the prescription safety network program. The prescriber identifier in the healthcare transaction can be compared to the list of deactivated prescribers in the REMS database 195 to determine if a match exists. If a match exists, a notification of denial may be generated and transmitted back to the pharmacy computer. If a match does not exist, a notification of authorization may be generated and transmitted back to the pharmacy computer.

In other example embodiments, yet another comparison may be made by the service provider computer. For example, the patient identifier, medication/product identifier, and prescriber identifier in the healthcare transaction may be compared to a historical database of approved claims, such as the historical claims database 196, to determine if the patient is receiving the current prescription from the same prescriber that previously prescribed that particular medication/product to the patient. If a record is identified that includes the same patient identifier and medication identifier but a different prescriber identifier, it may be indicative of the patient using several different doctors to obtain the same medication (e.g., doctor shopping) and may further be indicative of some type of fraud. If the prescriber identifier is different, it may also open up the possibility that the current prescriber may not be enrolled in the prescription safety network program. In situations where the prescriber identifier is different, the healthcare transaction may be rejected by the service provider computer. The rejected healthcare transaction may be transmitted back to the pharmacy computer where a pharmacist may be given the opportunity to override the rejection by resubmitting the healthcare transaction with, for example, an override code. In addition, or alternatively, the rejected healthcare transaction may be transmitted to a prescriber computer associated with, or otherwise communicated to the prescriber identified in the healthcare transaction, who can also override the rejection via an authorization. In this situation, the medication/product order history may be switched to the current prescriber in the historical claims database. If there is no record of the patient or the patient and medication in the historical claims database, or if the matching records include a match of the prescriber identifier, an approval response to the healthcare transaction may be generated and electronically transmitted back to the pharmacy computer.

The pharmacist, upon viewing the approval, may generate a second healthcare transaction, such as a prescription claim transaction, and may electronically transmit the second healthcare transaction to the service provider computer. The service provider computer may determine the claims processor for second healthcare claim transaction based on information therein and may electronically transmit the second healthcare claim transaction to the proper claims processor computer for adjudication.

After adjudicating the second healthcare transaction, the service provider computer may receive the adjudicated response from the claims processor computer and may forward the adjudicated response to the pharmacy computer. In certain alternate embodiments, rather than two separate healthcare transactions being submitted by the pharmacist via the pharmacy computer a single healthcare transaction may be submitted. In this alternate embodiment, rather than transmitting an approval response to the pharmacy computer once the determination is made that the requirements for the prescription safety network have been satisfied, the healthcare transaction may be electronically transmitted to a claims processor computer for adjudication. The healthcare transaction may then be adjudicated by the claims processor computer and transmitted back the pharmacy computer via the service provider computer. If the adjudicated response is an approval of the second healthcare transaction, the pharmacist may dispense the medication/product to the patient.

System Overview

FIG. 1 illustrates an example system 100 supporting healthcare transactions, electronic prescription ordering activities, prescription billing activities, and patient coverage eligibility verifications according to one example embodiment. The exemplary system 100 facilitates determining eligibility in a prescription safety network program as part of the processing of a healthcare transaction, including, but not limited to, an eligibility verification request, predetermination of benefits transaction, prescription claim transaction, prescription claim or billing request, healthcare order transaction, or e-prescription transaction (e.g., electronic prescription order transaction, e-script, or e-prescription), and will now be described illustratively with respect to FIG. 1. As shown in FIG. 1, the system 100 may include at least one healthcare provider computer 104, at least one service provider computer 106, at least one enrollment and validation engine 112, and at least one claims processor computer 108. As shown in FIG. 1, multiple healthcare provider computers 104A and 104B are presented by way of example and may be referred to individually or collectively as "healthcare provider computer 104" hereinafter. Alternatively, each of the pharmacy/healthcare provider computer 104A and prescriber/healthcare provider computer 104B may be specifically discussed with reference to designations on FIG. 1.

As desired, each of the healthcare provider computers 104A and 104B, service provider computer 106, enrollment and validation engine 112, and/or claims processor computer 108 may include one or more processing devices that may be configured for accessing and reading associated computer-readable media having stored thereon data and/or computer-executable instructions for implementing various methods, including those described herein.

In certain example embodiments, the service provider computer 106 may be in communication with or otherwise have access to the historical claims database 196. Additionally, in certain exemplary embodiments, the service provider computer 106 may be in communication with the enrollment and validation engine 112, which may access and/or be in communication with multiple suitable data storage devices, such as the physician REMS database 194 and the REMS database 195. While FIG. 1 shows the enrollment and validation engine 112 as being separate from the service provider computer 106, in certain example embodiments, the enrollment and validation engine 112 is part of the service provider computer 106 and sending and receiving between the two are internal transmissions within the service provider computer 106. Furthermore, while FIG. 1 shows the enrollment and validation engine 112 as a single module, in certain example embodiments, the functions/operations discussed below with regard to the enrollment and validation engine 112 may be completed by multiple modules, all or a portion of which may be part of the service provider computer 106. In certain example embodiments, the system 100 may include a physician enrollment and validation engine (not shown) that is separate from the enrollment and validation engine 112. In some of these embodiments, the physician REMS database 194 may be in communication with the physician enrollment and validation engine but not with the enrollment and validation engine 112.

Generally, network devices and systems, including one or more of the healthcare provider computers 104A and 104B, service provider computer 106, enrollment and validation engine 112, and claims processor computer 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the pharmacy computer 104A, prescriber computer 104B, service provider computer 106, claims processor computer 108, and the enrollment and validation engine 112 may be in communication with each other via one or more networks, such as network 110, which as described below can include one or more separate or shared private and public networks, including the Internet or a publicly switched telephone network. Each of these components—the pharmacy computer 104A, prescriber computer 104B, service provider computer 106, claims processor computer 108, enrollment and validation engine 112, and the network 110 will now be discussed in further detail.

Each healthcare provider computer 104 may be associated with a healthcare provider, such as, for example, a pharmacy, physician's office, hospital, clinic, hospice, etc. While the exemplary healthcare provider computers 104A and 104B reference and can be located within a pharmacy (104A) and an office/facility for a prescriber (104B) this is for example only and is not intended to be limiting in any manner. Each healthcare provider computer 104A and 104B may be any suitable processor-driven device that facilitates the processing of healthcare requests made by patients, consumers, or prescribers and the communication of information associated with healthcare transactions to the service provider computer 106, such as a server computer, a mainframe computer, one or more networked computers, a desktop computer, a personal computer, a digital assistant, a personal digital assistant, a digital tablet, an Internet appliance, an application-specific circuit, microcontroller, minicomputer, or any other processor-based device. In certain example embodiments, each healthcare provider computer 104A and 104B may be a suitable point of sale device associated with a healthcare provider. The execution of the computer-implemented instructions by either healthcare provider computer 104A or 104B may form a special purpose computer or other particular machine that is operable to facilitate the processing of healthcare requests made by patients and the communication of healthcare transactions to a service provider computer 106. Additionally, in certain example embodiments of the disclosure, the operations and/or control of each of the pharmacy computer 104A and the prescriber computer 104B may be distributed amongst several processing components.

In addition to each healthcare provider computer 104A and 104B having one or more processors 124A and 124B, each healthcare provider computer 104A and 104B may also include one or more memory devices 126A and 126B, one or more input/output ("I/O") interfaces 128A and 128B, and one or more network interfaces 130A and 130B. The memory devices 126A and 126B may be any suitable memory device, for example, caches, read-only memory devices, random access memory devices, magnetic storage devices, removable storage devices, etc. The memory devices 126A and 126B may store data, executable instructions, and/or various program modules utilized by each respective pharmacy computer 104A and prescriber computer 104B, for example, data files 132A and 132B, an operating system ("OS") 134A and 134B, and/or a client module 138A and 138B, respectively. Each of the data files 132A and 132B may include any suitable data that facilitates the receipt and/or processing of healthcare requests by the respective healthcare provider computer 104A and 104B and the generation and/or processing of healthcare transactions that are communicated to the service provider computer 106. For example, the data files 132A and 132B may include, but are not limited to, healthcare information and/or contact information associated with one or more patients, information, such as identifying and contact information, for a particular healthcare provider and/or the respective healthcare provider computer 104A and 104B, information associated with the service provider computer 106, information associated with one or more claims processors, and/or information associated with one or more healthcare transactions. The OS 134A and 134B may be any suitable software module that controls the general operation of the respective healthcare provider computer 104A and 104B. The OS 134A and 134B may also facilitate the execution of other software modules by the one or more respective processors 124A and 124B, for example, the client module 138A and 138B. The OS 134A and 134B may be any currently existing or future-developed operating system including, but not limited to, Microsoft Windows®, Apple OSX™, Linux, Unix, or a mainframe operating system.

Each client module 138A and 138B may be, for example, an Internet browser or other suitable software, including a dedicated program, for interacting with the service provider computer 106. For example, a user 120, such as a pharmacist, pharmacy assistant, or other pharmacy employee at the pharmacy computer 104A or a physician, nurse practitioner, nurse, or other, hospital or physician's office employee for the prescriber computer, may utilize the respective client module 138A and 138B in accessing and enrolling themselves or patients in one or more prescription safety network programs and/or preparing and providing a healthcare transaction, such as an eligibility verification request, a predetermination of benefits request, prescription claim transaction, prescription claim or billing request, healthcare order transaction, or e-prescription transaction (e.g., electronic prescription order transaction, e-script, or e-prescription), to the service provider computer 106 for delivery to: i) the appropriate claims processor computer 108 or other third-party for adjudication or other coverage/benefits determination, ii) the enrollment and validation engine 112 to enroll and/or determine eligibility requirements for a prescription safety network program are met, or iii) the appropriate other healthcare provider computer, such as from the prescriber computer 104B to a pharmacy computer 104A for dispensing of the prescribed medication. Each healthcare provider computer 104A and 104B may also utilize the respective client module 138A and 138B to retrieve or otherwise receive data, messages, or responses from the service provider computer 106, the enrollment and validation engine 112, and/or other components of the system 100. For example, in certain example embodiments, the client module 138A and 138B may be utilized to receive a response to an eligibility verification request, a healthcare transaction, an adjudicated response to the healthcare transaction, and/or a prescription fill status notification from the service provider computer 106 and/or the enrollment and validation engine 112, as will be described below.

The one or more I/O interfaces 128A and 128B may facilitate communication between the respective healthcare provider computer 104A and 104B and one or more input/output devices, for example, one or more user interface devices, such as, a keyboard, mouse, display, keypad, control panel, touch-screen display, remote control, microphone, etc., that facilitate user interaction with the particular healthcare provider computer 104A and 104B. For example, the one or more I/O interfaces 128A and 128B may facilitate entry of information associated with a healthcare transaction by an employee 120 of a healthcare provider, such as a pharmacy employee, pharmacist, physician, nurse, hospital employee, nurse practitioner, or the like affiliated with a pharmacy, hospital, physician's office, clinic, or other similar healthcare provider. The one or more network interfaces 130A and 130B may facilitate connection of the particular healthcare provider computer 104A and 104B to one or more suitable networks, for example, the network 110 illustrated in FIG. 1. In this regard, each healthcare provider computer 104A and 104B may receive and/or communicate information to other network components of the system 100, such as the service provider computer 106.

With continued reference to FIG. 1, the service provider computer 106 may include, but is not limited to, any suitable processor-driven device that is configured for receiving, processing, and fulfilling requests from the healthcare provider computers 104A and/or 104B, the enrollment and validation engine 112, and/or the claims processor computer 108 relating to pharmacy benefits, billing, electronic prescription submission, and/or other healthcare transactions and/or other activities. In certain exemplary embodiments, the service provider computer 106 may be a switch/router that routes healthcare transactions and/or other healthcare requests from healthcare provider computers 104 to the enrollment and validation engine 112 and/or the correct one of many claims processor computers 108. For example, the service provider computer 106 may route healthcare transactions communicated from one of the healthcare provider computers 104A and 104B to a claims processor computer 108, such as a pharmacy benefits manager (PBM), an insurer, a Medicare payor, a Medicare Part D payor, accountable care organization, or other third-party payor. In another example, the service provider computer 106 may route enrollment requests from a pharmacy computer 104A and/or a prescriber computer 104B to the enrollment and validation engine 112.

In certain example embodiments, the service provider computer 106 may include a suitable host server, host module 154, or other software that facilitates the receipt of enrollment requests and/or a healthcare transaction from a healthcare provider computer 104A and 104B and/or the routing of the received enrollment request to the enrollment and validation engine 112 or the received healthcare transaction to a claims processor computer 108. Any number of healthcare provider computers 104A and 104B, enrollment and validation engines 112, and/or claims processor computers 108 may be in communication with the service provider computer 106 as desired in various embodiments.

The service provider computer 106 may include any number of special purpose computers or other particular machines, application-specific circuits, microcontrollers, personal computers, minicomputers, mainframe computers, servers, networked computers, and/or other processor-driven devices. In certain example embodiments, the operations of the service provider computer 106 may be controlled by computer-executed or computer-implemented instructions that are executed by one or more processors associated with the service provider computer 106 to form a special-purpose computer or other particular machine that is operable to facilitate the receipt, routing, and/or processing of enrollment requests and/or healthcare transactions. The one or more processors that control the operations of the service provider computer 106 may be incorporated into the service provider computer 106 and/or in communication with the service provider computer 106 via one or more suitable networks. In certain exemplary embodiments, the operations and/or control of the service provider computer 106 may be distributed amongst several processing components.

Similar to the pharmacy computer 104A and prescriber computer 104B described above, the service provider computer 106 may include one or more processors 140, one or more memory devices 142, one or more input/output ("I/O") interface(s) 144, and one or more network interface(s) 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider 106, for example, data files 148, an operating system ("OS") 150, the host module 154, a service provider module 156, and a database management system ("DBMS") 152 to facilitate management of data files 148, the historical claims database 196, and other data stored in the memory devices 142. The OS 150 may be any currently existing or future-developed operating system including, but not limited to, Microsoft Windows®, Apple OSX™, Linux, Unix, or a mainframe operating system. The OS 150 may be a suitable software module that controls the general operation of the service provider computer 106 and/or that facilitates the execution of other software modules.

The service provider module 156 may be operable to perform one or more pre-edits or pre-analysis on a received healthcare transaction prior to routing or otherwise communicating the received healthcare transaction, such as a healthcare claim transaction, to a suitable claims processor computer 108 or an e-prescription transaction to a suitable pharmacy/healthcare provider computer 104A. Additionally, the service provider module 156 may be operable to perform one or more post-edits on an adjudicated reply or response that is received from a claims processor computer 108 for a healthcare transaction prior to routing the adjudicated response to one of the healthcare provider computers 104A and 104B. Further, the service provider module 156 may be operable to receive and route enrollment requests from one or more healthcare provider computers 104A and 104B to the enrollment and validation engine 112. Still further, the service provider module 156 may be operable to receive and evaluate a healthcare transaction to determine if the healthcare transaction includes a request for a medication/product that is under a prescription safety network program prior to routing the healthcare transaction to the enrollment and validation engine 112 for evaluation. In yet other example embodiments, the service provider module 156 may be operable to compare information from previous healthcare transactions with information in a current healthcare transaction to detect potential abuse or diversion. In certain example embodiments, the service provider module 156 may also be operable to perform the functions described with references to the enrollment and validation engine 112 herein. A wide variety of different pre-edits and/or post-edits may be performed by the service provider module 156 as desired in various embodiments of the disclosure.

According to one exemplary embodiment, the data files 148 may store healthcare transaction records associated with communications received from various healthcare provider computers 104A and 104B, enrollment and validation engine 112, and/or various claims processor computers 108. The data files 148 may also store any number of suitable routing tables that facilitate determining the destination of communications received from a healthcare provider computer 104A and 104B, the enrollment and validation engine 112, and/or the claims processor computer 108.

The exemplary data files 148 may also store records containing, for example, tables, schedules, or lists of patient identification data (e.g., patient first name, patient last name, patient social security number or healthcare insurance claim number (HICN number), cardholder ID and/or person code for the patient) and medication/product identification data (e.g., National Drug Code (NDC code) medication/product name and/or other medication/product identifier) for patients, healthcare transactions received for the patient, and an identification of whether the medication/product is part of a prescription safety network program.

The host module 154 may receive, process, and respond to requests from the client module 138 of one of the healthcare provider computers 104A and 104B, and may further receive, process, and respond to requests of the host module 192 of the enrollment and validation engine 112 and/or the host module 172 of the claims processor computer 108. For example, in embodiments where the enrollment and validation engine 112 is provided separately from the service provider computer 106, the host module 154 may route eligibility verification requests (or other healthcare transactions) to the enrollment and validation engine 112 for validation that the requirements of a prescription safety network program have been met, as described herein. The service provider computer 106 may include additional program modules for performing other processing methods described herein. Those of ordinary skill in the art will appreciate that the service provider computer 106 may include alternate and/or additional components, hardware, or software without departing from exemplary embodiments disclosed herein.

With continued reference to the service provider computer 106, the one or more I/O interfaces 144 may facilitate communication between the service provider computer 106 and one or more input/output devices, for example, one or more user interface devices, such as a keyboard, mouse, display, keypad, control panel, touch-screen display, remote control, microphone, etc. that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with any other components of the system 100.

The enrollment and validation engine 112 of FIG. 1 may include a processor-driven device that is configured for enrolling or otherwise qualifying prescribers or other healthcare providers, pharmacies/pharmacists, and/or patients for prescribing, dispensing, and/or using one or more prescribed or regulated medications/products. For example, registration or enrollment may occur by a prescriber, pharmacy, pharmacist, and/or patient accessing the enrollment and validation engine 112 via a call center or interactive voice response (IVR) system that communicates with the enrollment and validation engine 112. Alternatively, enrollment may also occur by a physician, pharmacy, pharmacist, and/or patient/caregiver accessing the enrollment and validation engine 112 via a network or Internet portal/website, such as through the use of a healthcare provider computer 104 and the network 110. Additionally, the enrollment and validation engine 112 may include one or more business rules for validating eligibility verification requests or other healthcare transactions associated with filling and refilling prescriptions for one or more medications/products.

In certain example embodiments, as discussed above, the system includes a physician enrollment and validation engine (not shown) that is separate from the enrollment and validation engine 112. In such an embodiment, the enrollment and validation engine 112 will not be configured for enrolling or otherwise qualifying prescribers for prescribing one or more prescribed or regulated medications/products. Instead, the physician enrollment and validation engine is configured for enrolling or otherwise qualifying prescribers for prescribing one or more prescribed or regulated medications/products. For example, registration or enrollment of the prescriber only may occur by the prescriber accessing the physician enrollment and validation engine via a call center or interactive voice response (IVR) system that communicates with the physician enrollment and validation engine. Alternatively, enrollment of the prescriber may also occur by prescriber accessing the physician enrollment and validation engine via a network or Internet portal/website, such as through the use of a prescriber computer 104B and the network 110. Upon enrollment, the physician enrollment and validation engine may store the prescriber enrollment information in the physician REMS database 194 communicably coupled to the physician enrollment and validation engine. Further, the physician enrollment and validation engine may provide the prescriber with log-in access to enroll patients in the REMS database 195 by providing, for example, user name and passwords that allow the prescriber to enroll a patient into a REMS database 195 for a particular prescription safety network program.

It will be appreciated that while the enrollment and validation engine 112 is presented as a single processor-driven device, the engine 112 may also be two or more distinct processor-driven devices for performing the respective enrollments and validations, according to certain example embodiments. The example enrollment and validation engine 112 may include computer-executable instructions for receiving and processing enrollment requests, healthcare transactions, and/or healthcare transaction data from a pharmacy computer 104A, prescriber computer 104B, service provider computer 106, or other third-party computer (such as a computer associated with a wholesale distributor of medications and/or products to pharmacies).

Similar to other components of the system 100, the enrollment and validation engine 112 may include one or more processors 178, one or more memory devices 180, one or more I/O interfaces 182, and one or more network interfaces 184. The one or more memory devices 180 may be any suitable memory devices, for example, caches, read only memory devices, random access memory devices, magnetic storage devices, removable memory devices. The one or more memory devices may store data, executable instructions, and/or various program modules utilized by the enrollment and validation engine 112, for example, data files 186, an OS 188, a DBMS 190, and a host module 192. The data files 186 may include any suitable information that is utilized by the enrollment and validation engine 112 to receive, process, analyze, and/or store enrollment information, prescription safety network program requirements, and/or educational materials. The OS 188 may be a suitable software module that controls the general operation of the particular enrollment and validation engine 112. The OS 188 may also facilitate the execution of other software modules by the one or more processors 178, for example, the DBMS 190 and/or the host module 192. The OS 188 may be any currently existing or future-developed operating system including, but not limited to, Microsoft Windows®, Apple OSX™, Linux, Unix, or a mainframe operating system. The DBMS 190 may be a suitable software module that facilitates access and management of one or more databases, such as the physician REMS database 194, and the REMS database 195, that are utilized to store information that is received by or utilized by the enrollment and validation engine 112 and/or the service provider computer 106. In some example embodiments, the one or more databases may be maintained separate from each other, such that the databases must be queried separately. For example, the data in the physician REMS database 194 may not be accessible to a query directed to the REMS database 195. In yet other embodiments, one or more of the databases may be maintained by another component of the system 100, such as a separate physician enrollment and validation engine (not shown). The host module 192 may initiate, receive, process, analyze, store, and/or respond to requests, such as enrollment requests, eligibility verification requests, and predetermination of benefits transactions from the host module 154 of the service provider computer 106, the client modules 138A and 138B of the pharmacy computer 104A or prescriber computer 104B respectively, or the client modules of another third-party computer seeking to enroll in a prescription safety network program. The enrollment and validation engine 112 may include additional program modules as desired. Those of ordinary skill in the art will appreciate that the enrollment and validation engine 112 may include alternate and/or additional components, hardware or software without departing from example embodiments disclosed herein.

The one or more I/O interfaces 182 may facilitate communication between the enrollment and validation engine 112 and one or more input/output devices, for example, one or more user interface devices, such as a keyboard, mouse, display, keypad, control panel, touch-screen display, remote control, microphone, etc. that facilitate user interaction with the enrollment and validation engine 112. The one or more network interfaces 184 may facilitate connection of enrollment and validation engine 112 to one or more suitable networks, for example, the network 110, a call center, an IVR system, or other network portal/website. In this regard, the enrollment and validation engine 112 may receive enrollment requests, enrollment information, healthcare transactions, healthcare transaction data, and/or other communications from the service provider computer 106, the pharmacy computer 104A, the prescriber computer 104B, and/or another third-party computer.

The physician REMS database 194 may be operable to store enrollment information for prescribers in one or more prescription safety network programs. In one example embodiment, the prescriber enrollment information is stored in a separate database, the physician REMS database 194, from that of the other parties enrolling in the prescription safety network program. Separating the prescriber enrollment data allows for improved privacy with regard to the prescriber data as it is not linked to the other enrollment data in the REMS database 195 and is not evaluated as part of the determination as to whether the requirements for the prescription safety network program have been satisfied. The prescriber enrollment information may include, but is not limited to, tables, schedules, or lists of prescriber identification data (e.g., the prescriber's name, address, phone number, and DEA number), an indication that the prescriber has satisfied the requirements for the particular prescription safety network program (e.g., verification from the prescriber that he/she has reviewed the educational materials and agrees to educate and enroll new patients who are prescribed medications/products within the program, and the identification of one or more prescription safety network programs that the prescriber is enrolled in). The prescriber identification data and prescription safety network programs in the physician REMS database 194 may be added, modified, accessed and/or evaluated by the enrollment and validation engine 112, a separate physician enrollment and validation engine (not shown), and/or the service provider computer 106. In some embodiments, the physician REMS database 194 may store enrollment information for any prescriber enrolled in a prescription safety network program. In these embodiments, the physician REMS database 194 may store information with each enrolled prescriber indicating the one or more prescription safety network programs for which the prescriber is enrolled.

The REMS database 195 may be operable to store enrollment information for patients, pharmacies/pharmacists, and/or wholesale distributors in one or more prescription safety network programs. The REMS database 195 may also include prescriber identifiers (e.g., DEA numbers) for prescribers who are no longer enrolled or otherwise no longer have rights to prescribe medication under the particular prescription safety network program. The pharmacy/pharmacist enrollment information may include, but is not limited to, tables, schedules, or lists of pharmacist identification data (e.g., the pharmacist's name, address, phone number, and NPI number), an indication that the pharmacist has satisfied the requirements for the particular prescription safety network program (e.g., verification from the pharmacist that he/she has reviewed the educational materials and agrees to not resell the medication/product to another retail entity and educate new patients who are prescribed medications/products within the program, and the identification of one or more prescription safety network programs that the pharmacist is enrolled in). In an alternative embodiment, the enrollment information for the pharmacists may be stored in a different database (not shown) separate from the patient enrollment information and the wholesale distributor enrollment information in the REMS database 195, and still separate from the prescriber enrollment information in the physician REMS database 194. Further, this alternative embodiment may provide the pharmacist with enrollment access right such that the pharmacist could enroll patients into the REMS database 195 when the patient is prescribed a medication/product in a prescription safety network program. By giving the pharmacist enrollment access rights for patients in the REMS database 195, the determination of a patient in the REMS database 195 would, in certain example embodiments, eliminate the need to determine if the pharmacist in a healthcare transaction is also enrolled in the prescription safety network program, because the patient could not be enrolled in that program unless an enrolled pharmacist enrolled that patient.

The patient enrollment information may be input into the REMS database 195 by a prescriber enrolled in at least one prescription safety network program and whose enrollment data is stored separately from and not linked in any manner to the data in the physician REMS database 194. By giving the prescriber enrollment access rights for patients in the REMS database 195, the determination of a patient in the REMS database 195 would, in certain example embodiments, eliminate the need to determine if the prescriber in a healthcare transaction is also enrolled in the prescription safety network program, because the patient could not be enrolled in that program unless an enrolled prescriber enrolled that patient. In one example embodiment, the patient enrollment information may include, but is not limited to, tables, schedules, or lists of patient identification data (e.g., patient first name, patient last name, patient social security number or Health Insurance Claim Number (HICN) number), cardholder ID and/or person code for the patient, phone number, and/or other insurance information for the patient), an indication that the patient has received the designated education with regard to the medication/product in the prescription safety network program, and the identification of one or more prescription safety network programs that the patient is enrolled in).

The wholesale distributor enrollment information may include, but is not limited to, tables, schedules, or lists of wholesale distributor identification data (e.g., the wholesale distributor's name, address, phone number, and NPI number), an indication that the wholesale distributor has satisfied the requirements for the particular prescription safety network program (e.g., verification from the wholesale distributor that it will verify enrollment in a prescription safety network program of a pharmacy/pharmacist requesting the purchase of a medication/product in a prescription safety network program prior to providing that medication/product to the pharmacy and will not sell product under the prescription safety network program to another wholesaler, and the identification of one or more prescription safety network programs that the wholesale distributor is enrolled in). In an alternative embodiment, the enrollment information for the wholesale distributors may be stored in a different database (not shown) separate from the patient enrollment information and the pharmacy/pharmacist enrollment information in the REMS database 195, and still separate from the prescriber enrollment information in the physician REMS database 194. Further, this alternative embodiment may provide the wholesale distributor with enrollment access right such that the wholesale distributor could enroll pharmacists/pharmacies (the pharmacists/pharmacies would not be able to self-enroll) into the REMS database 195 or another database when providing the pharmacist/pharmacy a medication/product in a prescription safety network program. By giving the wholesale distributor enrollment access rights for pharmacists/pharmacies as well as giving the prescriber enrollment access rights for the patient in the REMS database 195, in one example embodiment only the patient identification information would need to be matched in a healthcare transaction to determine if each of the prescriber, wholesale distributor, pharmacy, and patient are enrolled in the prescription safety network program. This is due to the following: i) as only the prescriber can enroll a patient in the prescription safety network program, the patient would not be in the program unless a prescriber for the patient was enrolled in the program as well; ii) as only the wholesale distributor can enroll a pharmacy/pharmacist in the prescription safety network program, the pharmacy would not be requesting to dispense a medication/product in the program unless the wholesaler had enrolled in the program and provided that medication/product to the pharmacy; and iii) only the pharmacy, via the pharmacy computer 104A, submits an eligibility verification request to the enrollment and validation engine 112 to determine if the requirements of the program have been satisfied, so no eligibility verification request could be made unless the pharmacy has access to the medication/product and therefore was enrolled in the prescription safety network program.

The historical claims database 196 may be operable to store information from prior healthcare transactions including, but not limited to, tables, schedules, or lists of patient identification data for patients (e.g., patient first name, patient last name, patient social security number or HICN number, cardholder ID and/or person code for the patient); tables, schedules, or lists of medication identifiers (e.g., the related NDC code, RxNorm number, and/or medication/product name) for the one or more prescribed products/medications identified in the healthcare transaction; and the prescriber identifier (e.g., DEA number) for the prescriber that prescribed the medication to the patient. The healthcare transaction, patient and prescription medication/product data in the historical claims database 196 may then be accessed and evaluated by the service provider computer 106.

With continued reference to FIG. 1, the claims processor computer 108 may be any suitable processor-driven device that facilitates receiving, processing, and/or fulfilling healthcare transactions, such as eligibility verification requests, predetermination of benefits transactions, prescription claim transactions, prescription claim or billing requests, healthcare order transactions, or e-prescription transactions (e.g., electronic prescription order transactions, e-scripts, or e-prescriptions) received from the service provider computer 106 and/or the enrollment and validation engine 112. For example, the claims processor computer 108 may be a processor-driven device associated with a pharmacy benefits manager (PBM), an insurer, a government payor, a Medicare Part D payor, accountable care organization, or a claims clearinghouse. As desired, the claims processor computer 108 may include any number of special purpose computers or other particular machines, application-specific circuits, microcontrollers, personal computers, minicomputers, mainframe computers, servers, and the like.

In certain exemplary embodiments, the operations of the claims processor computer 108 may be controlled by computer-executed or computer-implemented instructions that are executed by one or more processors associated with the claims processor computer 108 to form a special-purpose computer or other particular machine that is operable to facilitate the receipt, processing, and/or fulfillment of healthcare transaction requests and/or reversal transactions received from the service provider computer 106 and/or the enrollment and validation engine 112. The one or more processors that control the operations of the claims processor computer 108 may be incorporated into the claims processor computer 108 and/or in communication with the claims processor computer 108 via one or more suitable networks. In certain embodiments, the operations and/or control of the claims processor computer 108 may be distributed amongst several processing components.

Similar to other components of the system 100, the claims processor computer 108 may include one or more processors 158, one or more memory devices 160, one or more input/output ("I/O") interfaces 162, and one or more network interfaces 164. The one or more memory devices 160 may be any suitable memory devices, for example, caches, read-only memory devices, random access memory devices, magnetic storage devices, removable memory devices. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare transactions and/or reversal transactions, for example, patient profiles, patient insurance information (e.g., co-pay levels, deductible levels, groups of covered/uncovered products, etc.), other information associated with a patient, information associated with a healthcare provider, etc. The OS 168 may be a suitable software module that controls the general operation of the claims processor computer 108. The OS 168 may also facilitate the execution of other software modules by the one or more processors 158, for example, the DBMS 170 and/or the host module 172. The OS 168 may be any currently existing or future-developed operating system including, but not limited to, Microsoft Windows®, Apple OSX™, Linux, Unix, or a mainframe operating system.

The DBMS 170 may be a suitable software module that facilitates access and management of one or more databases that are utilized to store information that is utilized by the claims processor computer 108 in various example embodiments of the disclosure. The host module 172 may initiate, receive, process, and/or respond to requests, such as healthcare transactions, reversal transactions, or claim requests, from the host module 154 of the service provider 106 or from the host module 192 of the enrollment and validation engine 112. The claims processor computer 108 may include additional program modules for performing other pre-processing or post-processing methods described herein. Those of ordinary skill in the art will appreciate that the claims processor computer 108 may include alternate and/or additional components, hardware or software without departing from the example embodiments described herein.

The one or more I/O interfaces 162 may facilitate communication between the claims processor computer 108 and one or more input/output devices, for example, one or more user interface devices, such as a keyboard, mouse, display, keypad, control panel, touch-screen display, remote control, microphone, etc. that facilitate user interaction with the claims processor computer 108. The one or more network interfaces 164 may facilitate connection of the claims processor computer 108 to one or more suitable networks, for example, the network 110. In this regard, the claims processor computer 108 may receive healthcare transactions, reversal transactions, and/or other communications from the service provider computer 106 and/or the enrollment and validation engine 112, and the claims processor computer 108 may communicate information associated with processing the healthcare transactions and/or reversal transactions to the service provider computer 106 and/or the enrollment and validation engine 112.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be transmitted between or among the healthcare provider computers 104A and 104B, the service provider computer 106, the enrollment and validation engine 112, and/or the claims processor computer 108. Due to network connectivity, various methodologies, as described herein may be practiced in the context of distributed computing environments. Although the service provider computer 106 is shown for simplicity as being in communication with the healthcare provider computers 104A and 104B, the enrollment and validation engine 112, or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with one example embodiment. For example, the service provider computer 106 may form the basis of network 110 that interconnects one or more of the healthcare provider computers 104A and 104B, the enrollment and validation engine 112, and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one exemplary embodiment, the service provider computer 106 (or other computer) may be implemented as a specialized processing machine that includes hardware and/or software for performing the methods described herein. In addition, at least a portion of the processor and/or processing capabilities of the service provider computer 106 may be implemented as part of the claims processor computer 108 or the healthcare provider computer 104. In addition, at least a portion of the processor and/or processing capabilities of the healthcare provider computer 104, and/or the claims processor computer 108 may be implemented as part of the service provider computer 106. Further, in certain example embodiments the system may include other third-party computers/systems, such as a wholesale distributor computer associated with a wholesale distributor of medications/products in a prescription safety network program, that include elements similar to those described in the computer systems above and having access to the network 110 for enrolling in one or more prescription safety network programs. Accordingly, the exemplary embodiments described herein should not be construed as being limited to any particular operating environment, system architecture, or device configuration.

Operational Overview

Figure 2:
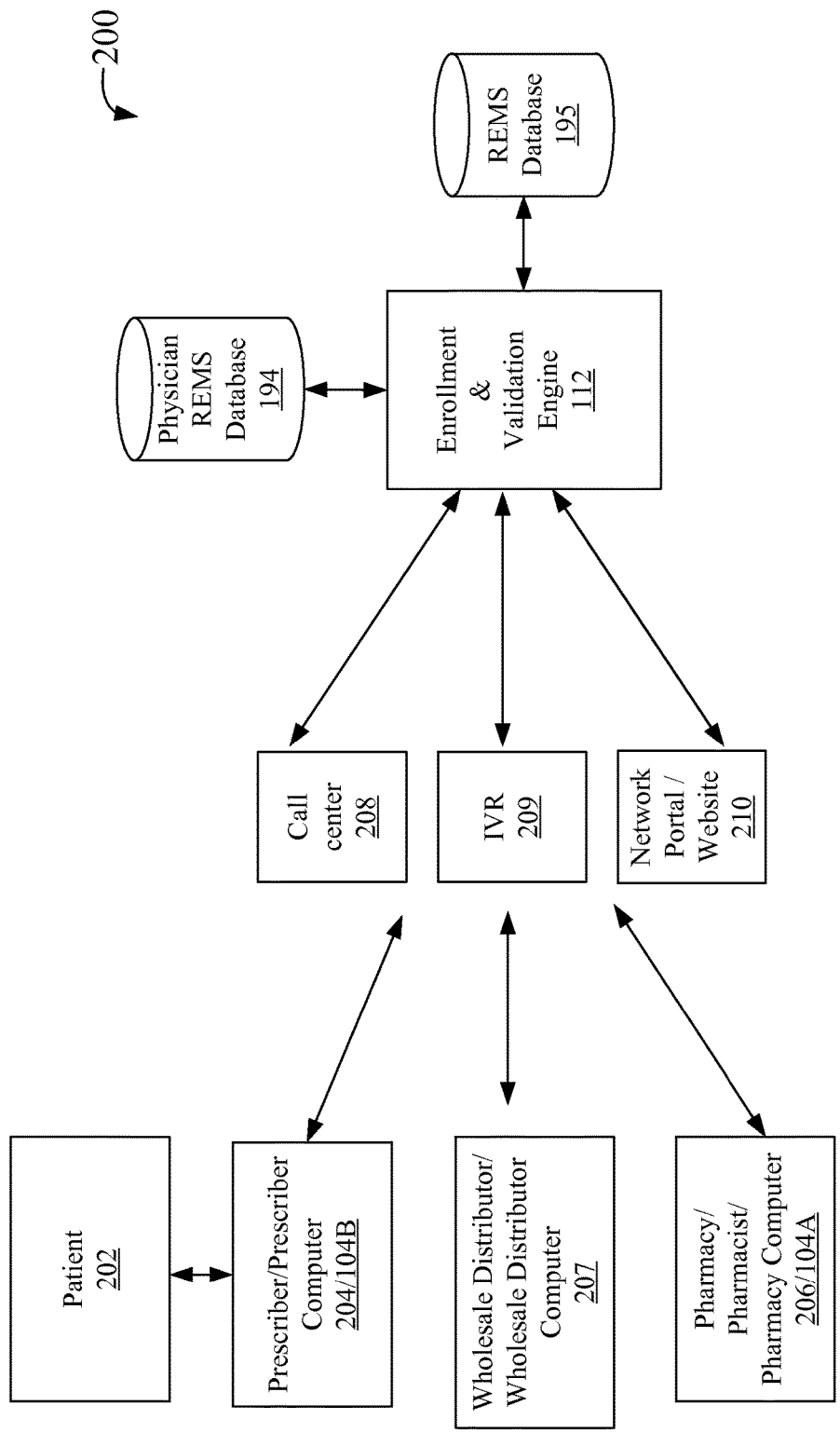
FIG. 2 is a diagram of an example data flow for enrollment of one or more of a patient, prescriber, pharmacy/pharmacist, and/or medication wholesale distributor in a prescription safety network program, according to one exemplary embodiment of the disclosure.

FIG. 2 is a diagram of one example data flow 200 for enrolling one or more of a patient, prescriber, pharmacy/pharmacist, and/or wholesale distributor of medication/products in one or more prescription safety network programs, such as through the service provider computer 106 and/or the enrollment and validation engine 112, according to one example embodiment of the disclosure. For example, enrollment may be necessary for a patient 202, prescriber 204, wholesale distributor 207 and/or pharmacy/pharmacist 206 to use, prescribe, ship, and/or dispense a particular medication/product, according to an example embodiment of the disclosure. As shown in FIG. 2, the prescriber 204, pharmacy/pharmacist 206, and/or wholesale distributor 207 may enroll in a prescription safety network program by communicating with the enrollment and validation engine 112 via a call center 208, an interactive voice response (IVR) system 209, or a network portal/website 210, such as with the prescriber computer 104B, the pharmacy computer 104A, or another third-party computer system.

In another example embodiment, the system includes a physician enrollment and validation engine (not shown) that is separate from the enrollment and validation engine 112. In such an embodiment, data flow 200 may be modified such that prescriber 204 does not enroll in the prescription safety network program by communicating with the enrollment and validation engine 112 but instead by communicating with the physician enrollment and validation engine via the call center 208, the IVR system 209, or the network portal/website 210. In one example, the prescriber 204 communicates with the physician enrollment and validation engine via the network portal/website through the use of the prescriber computer 104B. Upon enrollment, the physician enrollment and validation engine may store the prescriber enrollment information in the physician REMS database 194, which is accessible by or otherwise in communication with the physician enrollment and validation engine but not accessible by or otherwise in communication with the enrollment and validation engine 112.

Figure 3:
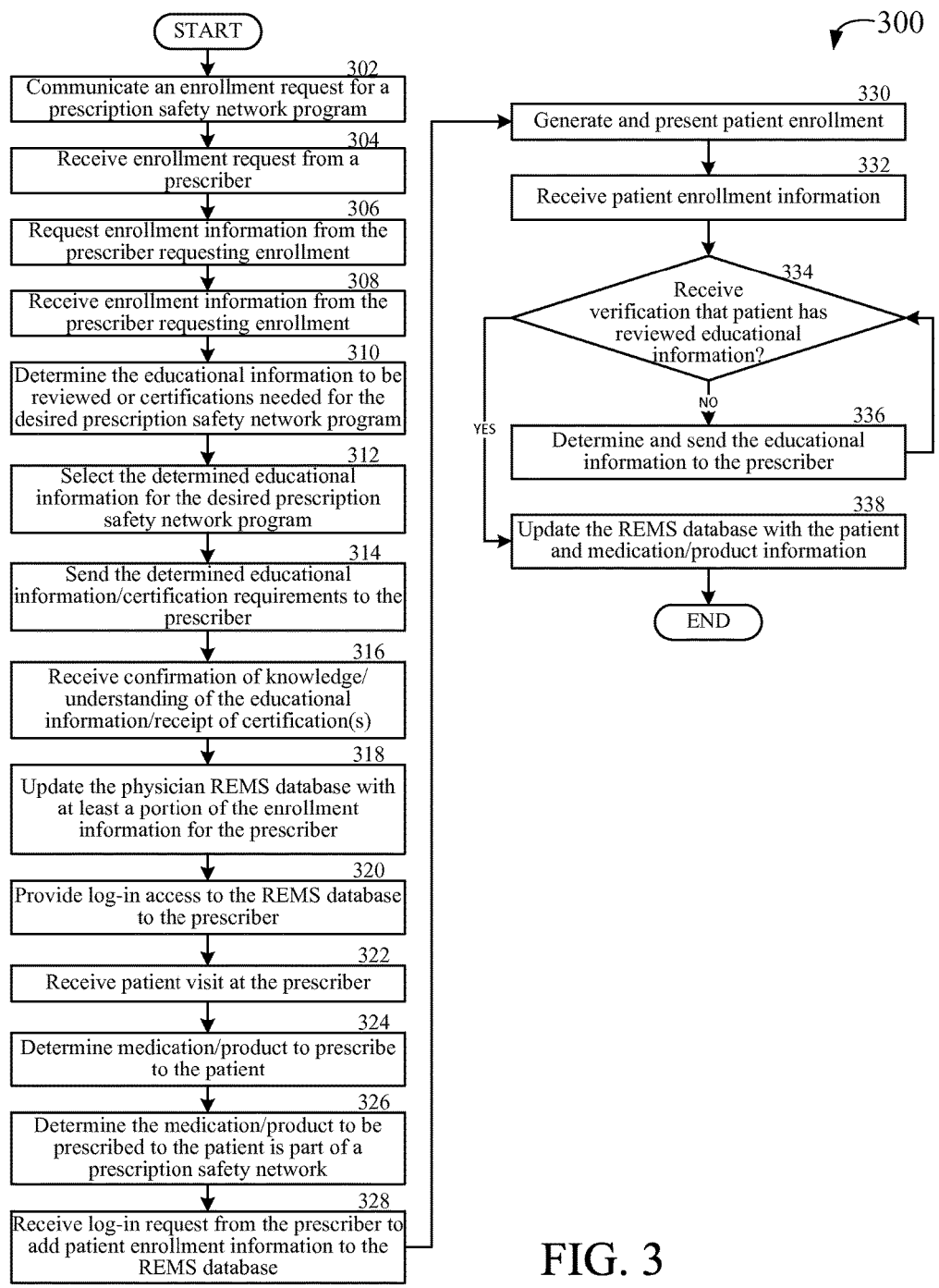
FIG. 3 is a flow chart of an example method for enrollment of a prescriber and/or patient in a prescription safety network program, according to one exemplary embodiment of the disclosure.

FIG. 3 is a flow chart of an example method 300 for enrollment of a prescriber and or patient 202 in a prescription safety network program, in accordance with one exemplary embodiment. Referring now to FIGS. 1-3, the exemplary method 300 begins at the START block and proceeds to block 302, where the prescriber 204 communicates an enrollment request for a prescription safety network program. In one example embodiment, the prescriber 204, via the prescriber computer 104B may transmit a request to the enrollment and validation engine 112 via the network portal 210 to enroll in the prescription safety network program. At block 304, the enrollment and validation engine 112 may receive the enrollment request from the prescriber 204 (such as by the prescriber computer 104B) via, for example, the network portal or website 210. In another example embodiment, the prescriber 204 may use a telephone to contact a call center 208 or IVR system 209 to enroll with the enrollment and validation engine 112 in the prescription safety network program. For example, the call center 208 may be staffed with one or more customer service representatives who can verbally receive enrollment information from the prescriber 204 and can transcribe that enrollment information into the enrollment and validation engine 112. In another example embodiment, an IVR system 209 may be responsive to touch-tone telephone inputs from the prescriber 204 to enroll. The IVR system 209 may also be capable of transcribing or recognizing received verbal inputs from the prescriber 204.

At block 306, the enrollment and validation engine 112 may generate and transmit a request for enrollment information to the prescriber 204 requesting enrollment. For example, the request may be transmitted via the network portal 210 to the prescriber computer 104B. In one example embodiment, the request may include one or more prescriber-fillable fields on a display of the prescriber computer 104B. Alternatively, the request for registration information may be presented to the prescriber 204 by the IVR 209 or a person at the call center 208. At block 308, the enrollment and validation engine 112 may receive enrollment information from the prescriber 204. In one example, the enrollment information for the prescriber 204 is received from the prescriber computer 104B via the network portal 210. Alternatively, the enrollment information may be received by the call center 208 or the IVR 209, which passes on the enrollment information to the enrollment and validation engine 112. In one example, the enrollment information may include, but is not limited to, the desired prescription safety network to enroll in, a medication/product identifier (e.g., NDC code or RxNorm code), the prescriber's DEA number, his/her office address, and desired method of communication (e.g., email address, phone number, etc.)

At block 310 the enrollment and validation engine 112 may determine the educational information that must be reviewed by the prescriber 204 prior to enrollment as well as any other requirements (e.g., certifications) necessary for the prescriber 204 to enroll in the prescription safety network program. In one example, the determination may be made using the medication/product identifier and/or the identification of the desired prescription safety network program in the enrollment information. In an alternative embodiment, the identification of the educational materials and/or the identification of other requirements for enrollment may be made by the call center 208 and/or the IVR 209. At block 312, the enrollment and validation engine 112 may select the determined educational materials, and at block 314 the enrollment and validation engine 112 may electronically transmit the educational material and/or other requirements to the prescriber computer 104B via the network portal 210. Alternatively, the educational material may be transmitted to the prescriber 204 by the call center 208 or the IVR 209 and may be sent via traditional mail, fax, email, or the like.

At block 316, a confirmation of knowledge/understanding of the educational materials and other requirements may be received from the prescriber computer 104B via the network portal 210 by the enrollment and validation engine 112. Alternatively, the confirmation of knowledge of the educational materials or completion of other requirements may be received at the call center 208 or IVR 209 from the prescriber 204. At block 318, the physician REMS database 194 is updated with at least a portion of the prescriber enrollment information. In one example, the enrollment and validation engine 112 stores the prescriber enrollment information in the physician REMS database 194. In an alternative embodiment, the physician REMS database 194 is updated to include at least a portion of the prescriber enrollment information by the call center 208 or IVR 209.

At block 320, log-in access to enroll patients in the REMS database 195 is provided to the prescriber 204. For example, the prescriber 204 can be assigned or can choose log-in information (a user name and password) to access the REMS database 195 and the log-in information can be received and stored by the enrollment and validation engine 112 from the prescriber computer 204 via the network portal 210. In certain example embodiments, the prescriber 204 may be provided enrollment access to the REMS database 195 in order to submit patient enrollment information for patients that the prescriber 204 prescribes a medication/product that is part of a prescription safety network program. At block 322, the prescriber 204 may receive a patient 202 for a medical visit. At block 324, the prescriber 204 may determine a medication/product to prescribe to the patient 202. The prescriber 204 may determine that the prescribed medication/product is part of a prescription safety network program at block 326.

At block 328, a log-in request from the prescriber 204 may be received from the prescriber computer 104B via the network portal 210 at the enrollment and validation engine 112 to add patient enrollment information to the REMS database 195. At block 330, the enrollment and validation engine 112 may generate and present a patient enrollment form at the prescriber computer 104B via the network portal 210. In one example embodiment, the patient enrollment form may include one or more user-fillable fields on a display at the prescriber computer 104B. At block 330, the enrollment and validation engine 112 may receive the patient enrollment information. In one example, the patient enrollment information may be received from the prescriber computer 104B via the network portal/website 210. In one example embodiment, the patient enrollment information may include, but is not limited to, patient identification data (e.g., patient first name, patient last name, patient social security number or Health Insurance Claim Number (HICN number), cardholder ID and/or person code for the patient, phone number, and/or other insurance information for the patient), an indication that the patient 202 has received the designated education with regard to the medication/product in the prescription safety network program, and the identification of one or more prescription safety network programs that the patient is enrolled in). In an alternative embodiment, the prescriber 204 may submit the patient enrollment information for the patient 202 to the enrollment and validation engine 112 for storage in the REMS database 195 through the call center 208 or the IVR 209.

At block 334, an inquiry is conducted to determine if a verification has been received that the patient 202 has reviewed or otherwise been explained the information in the educational materials for the prescription safety network program. In one example embodiment, the determination is made by the enrollment and validation engine 112 based on an evaluation of the patient enrollment information received from the prescriber 204 at the prescriber computer 104B. If not, the NO branch is followed to block 336, where the enrollment and validation engine 112 may determine the educational information that is to be reviewed by the patient 202 under the requested prescription safety network program and may transmit or otherwise facilitate the sending of the educational material to the prescriber 204. In one example embodiment, the educational material may be transmitted by the enrollment and validation engine 112 to the prescriber computer 104B via the network portal 104B.

Returning to block 334, if it is determined that verification has been received that the patient 202 has reviewed the educational materials, the YES branch may be followed to block 338, where the enrollment and validation engine 112 may store the patient enrollment information in the REMS database 195. The process may then continue to the END block.

Figure 4:
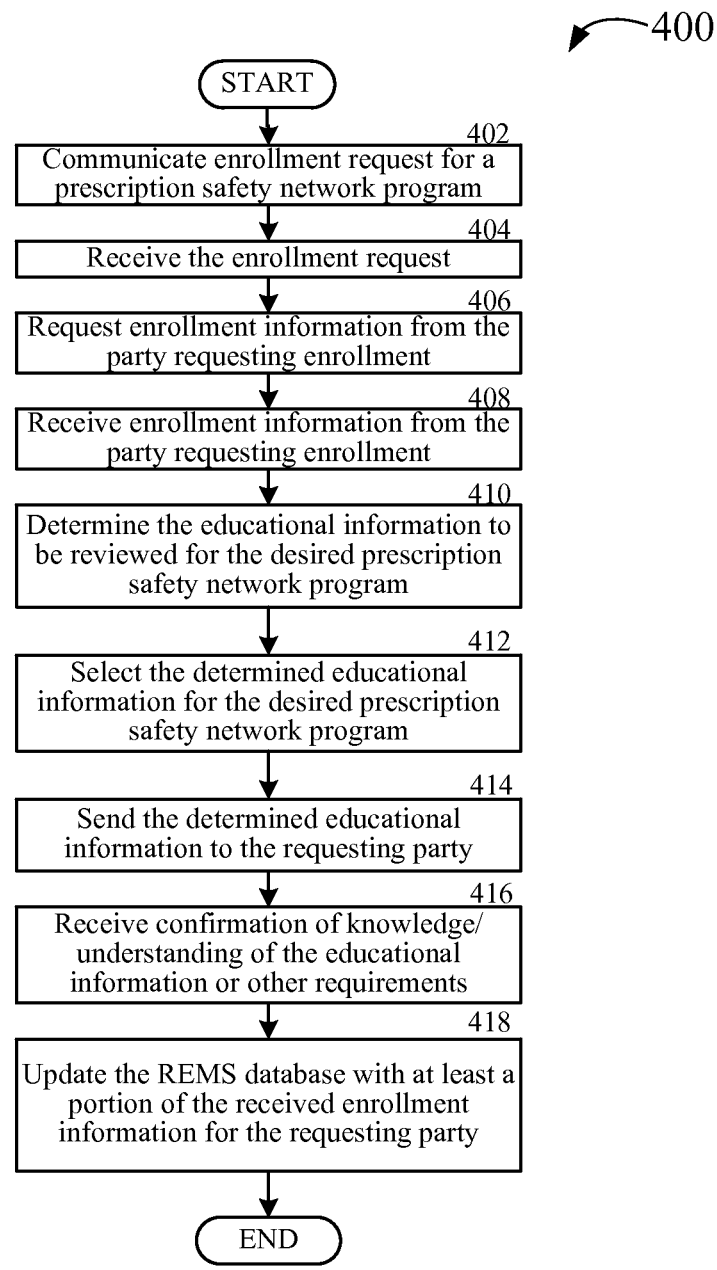
FIG. 4 is a flow chart of an example method for enrollment of pharmacies/pharmacists, medication wholesale distributors, or others in a prescription safety network program, according to one exemplary embodiment of the disclosure.

FIG. 4 is a flow chart of an example method 400 for enrollment of pharmacies/pharmacists, wholesale distributors of medications/products, or other third-parties in a prescription safety network program. Referring now to FIGS. 1, 2, and 4, the exemplary method 400 begins at the START block and proceeds to block 402, where the pharmacy/pharmacist 206, wholesale distributor 207, or another third party communicates an enrollment request for a prescription safety network program. In one example embodiment, the pharmacist 206, via the pharmacy computer 104A may transmit a request to the enrollment and validation engine 112 via the network portal 210 to enroll in the prescription safety network program. In another example embodiment, the wholesale distributor 207 may use a wholesale distributor computer to transmit the request to the enrollment and validation engine 112 to enroll the wholesale distributor 207 in the prescription safety network program. At block 404, the enrollment and validation engine 112 may receive the enrollment request from the pharmacist 206 or wholesale distributor 207 via, for example, the network portal or website 210. In another example embodiment, the pharmacist 206 and/or wholesale distributor 207 may use a telephone to contact a call center 208 or IVR system 209 to enroll with the enrollment and validation engine 112 in the prescription safety network program.

At block 406, the enrollment and validation engine 112 may generate and transmit a request for enrollment information to the pharmacy 206 at the pharmacy computer 104A or the wholesale distributor 207 at the wholesale distributor computer. For example, the request may be transmitted via the network portal 210 to the pharmacy computer 104A or the wholesale distributor computer. In one example embodiment, the request may include one or more form-fillable fields on a display of the pharmacy computer 104A or wholesale distributor computer. Alternatively, the request for registration information may be presented to the pharmacist 206 or wholesale distributor 207 by the IVR 209 or a person at the call center 208. At block 408, the enrollment and validation engine 112 may receive enrollment information from the pharmacist 206 or wholesale distributor 207. In one example, the enrollment information for the pharmacist 206 is received from the pharmacy computer 104A via the network portal 210. In another example embodiment, the enrollment information for the wholesale distributor may be received from the wholesale distributor computer via the network portal 210. Alternatively, the enrollment information may be received by the call center 208 or the IVR 209, which passes on the enrollment information to the enrollment and validation engine 112. In one example, the enrollment information for the pharmacy/pharmacist may include, but is not limited to, pharmacist identification data (e.g., the pharmacist's name, address, phone number, and NPI number), an indication that the pharmacist has satisfied the requirements for the particular prescription safety network program (e.g., verification from the pharmacist that he/she has reviewed the educational materials and agrees to not resell the medication/product to another retail entity and educate new patients who are prescribed medications/products within the program, and the identification of one or more prescription safety network programs that the pharmacist is enrolled in). Further, the enrollment information for the wholesale distributor may include, but is not limited to, wholesale distributor identification data (e.g., the wholesale distributor's name, address, phone number, and NPI number), an indication that the wholesale distributor has satisfied the requirements for the particular prescription safety network program (e.g., verification from the wholesale distributor that it will verify enrollment in a prescription safety network program of a pharmacy/pharmacist requesting the purchase of a medication/product in a prescription safety network program prior to providing that medication/product to the pharmacy and will not sell product under the prescription safety network program to another wholesaler, and the identification of one or more prescription safety network programs that the wholesale distributor is enrolled in).

At block 410 the enrollment and validation engine 112 may determine the educational information that must be reviewed by the pharmacist 206 prior to enrollment as well as any other requirements (e.g., certifications/verifications) necessary for the pharmacy 206 or wholesale distributor 207 to enroll in the particular prescription safety network program. In one example, the determination may be made using the medication/product identifier and/or the identification of the desired prescription safety network program in the enrollment information. In an alternative embodiment, the identification of the educational materials and/or the identification of other requirements for enrollment may be made by the call center 208 and/or the IVR 209. At block 412, the enrollment and validation engine 112 may select the determined educational materials, and at block 414 the enrollment and validation engine 112 may electronically transmit the educational materials and/or other requirements to the pharmacy computer 104A or wholesale distributor computer via the network portal 210. Alternatively, the educational materials may be transmitted to the pharmacy/pharmacist 206 or wholesale distributor 207 by the call center 208 or the IVR 209 and may be sent via traditional mail, fax, email, or the like.

At block 416, a confirmation of knowledge/understanding of the educational materials and other requirements may be received from the pharmacy computer 104A or wholesale distributor computer via the network portal 210 by the enrollment and validation engine 112. Alternatively, the confirmation of knowledge of the educational materials or completion of other requirements may be received at the call center 208 or IVR 209 from the pharmacist 206 or wholesale distributor. At block 418, the REMS database 195 is updated with at least a portion of the pharmacy/pharmacist enrollment information or wholesale distributor enrollment information. In one example, the enrollment and validation engine 112 stores the pharmacy/pharmacist enrollment information or wholesale distributor information in the REMS database 195. In an alternative embodiment, the REMS database 195 is updated to include at least a portion of the pharmacy/pharmacist enrollment information or wholesale distributor enrollment information by the call center 208 or IVR 209. In another alternative embodiment, the pharmacy/pharmacist enrollment information and/or the wholesale distributor enrollment information may be stored in other databases separate from each other and also separate from the patient enrollment information stored in the REMS database 195 and the prescriber enrollment information stored in the physician REMS database 194. The process may then continue to the END block.

While not shown in FIG. 4, in certain alternative example embodiments, the pharmacist 206, via the pharmacy computer 104A, may be provided with log-in access to enroll patients into prescription safety network programs in the REMS database 195 in a manner substantially similar to that described above with regard to the prescriber 204 in FIG. 3. Similarly, in certain alternative embodiments, the wholesale distributor 207 may be provided with log-in access to enroll pharmacies in prescription safety network programs in the REMS database 195 in a manner substantially similar to that described above with regard to the prescriber 204 in FIG. 3. In this alternative embodiment, the pharmacy/pharmacist would not need to or would not be allowed to enroll themselves into the prescription safety network program.

Figure 5:
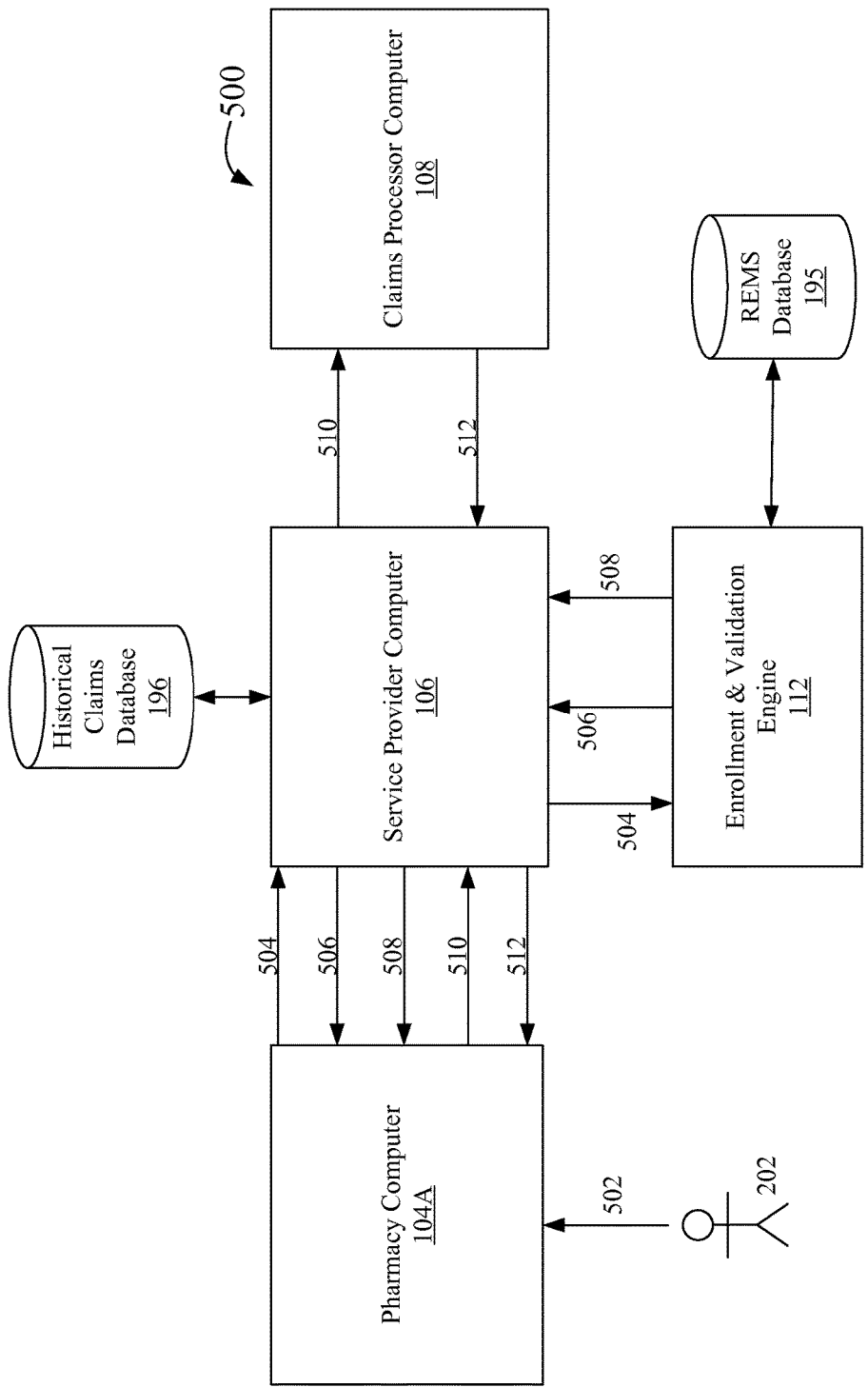
FIG. 5 is a diagram of an example data flow for determining a patient's eligibility to receive a medication/product in a prescription safety network program as part of the processing of a healthcare transaction, according to one exemplary embodiment of the disclosure.
Figure 6A:
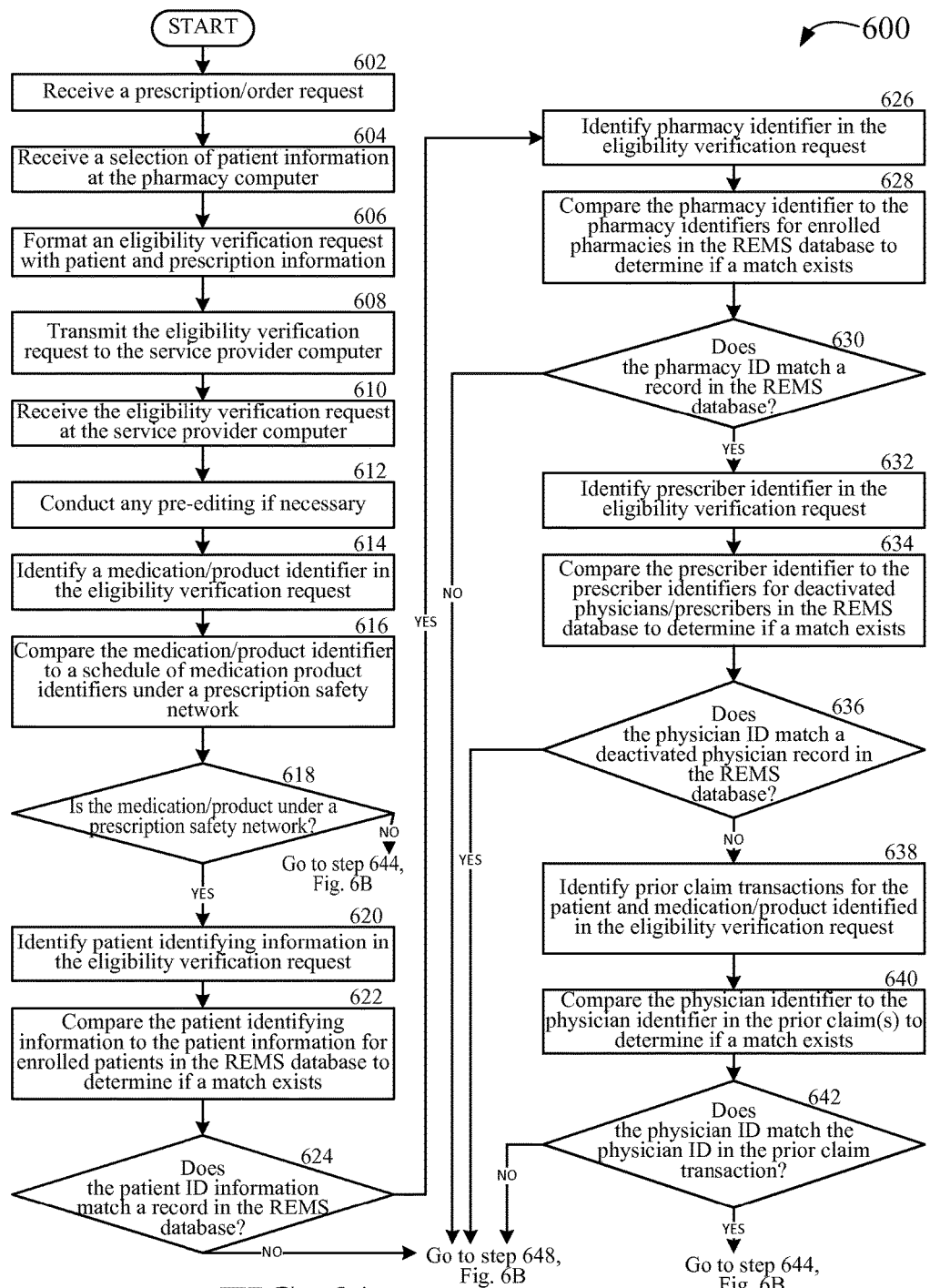
FIGS. 6A-B are a flow chart of an example method for determining a patient's eligibility to receive a medication/product in a prescription safety network program as part of the processing of a healthcare transaction, according to one exemplary embodiment of the disclosure.
Figure 6B:
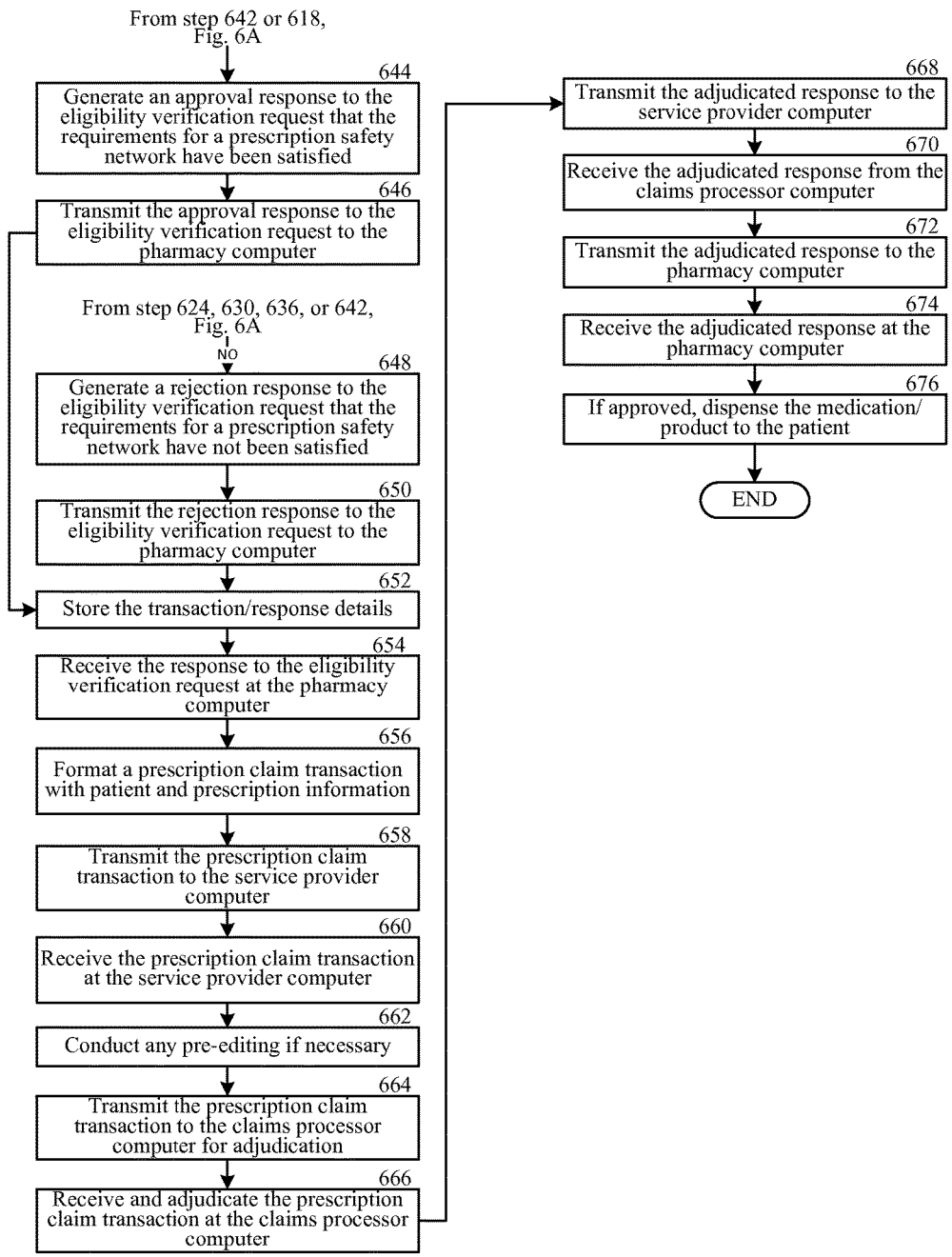

FIG. 5 is a diagram of an example data flow 500 for determining a patient's eligibility to receive a medication/product in a prescription safety network program as part of the processing of a healthcare transaction, according to one exemplary embodiment of the disclosure. FIGS. 6A-B are a flow chart of an example method 600 for determining a patient's eligibility to receive a medication/product in a prescription safety network program as part of the processing of a healthcare transaction (e.g., an eligibility verification request, a predetermination of benefits transaction, a prescription claim transaction, prescription claim or billing request, healthcare order transaction, or e-prescription transaction (e.g., electronic prescription order transaction, e-script, or e-prescription)), in accordance with one exemplary embodiment of the disclosure.

The exemplary method 600 will be described with reference to two healthcare transactions, the first being an eligibility verification request and the second being a prescription claim transaction. However, this is only for purposes of example as other healthcare transactions, which may include, for example, an eligibility verification request, a predetermination of benefits transaction, the healthcare claim transaction, prescription claim or billing request, healthcare order transaction, or e-prescription transaction (e.g., electronic prescription order transaction, e-script, or e-prescription) could be substituted for the eligibility verification request and/or the prescription claim transaction. In other example embodiments, a single healthcare transaction may be used to accomplish the goals of one or more of the above transactions. Each form of healthcare transaction should each individually be read as being used in the method described below.

Referring now to FIGS. 1, 5, and 6A-B, the exemplary method 600 begins at the START block and proceeds to block 602, where a prescription/order request 502 is received. In one example embodiment, the prescription/order request 502 is received by a pharmacist at a pharmacy. The prescription/order request 502 may be received from a patient 202, a prescriber prescribing a medication/product (e.g., physician, clinic, physician's office, hospital, or any other person legally permitted to prescribe medications, etc.), by phone, via the Internet, via an e-prescription transaction or by way of an electronic system order. For example, the prescription 502 may be received by the patient 202 from a prescriber of the medication, such as a doctor, dentist, nurse, physician's assistant, or any other person legally authorized to prescribe medications, products, and/or services for a patient 202. The patient 202 may go to the location of the pharmacy and physically hand the prescription request 502 to the pharmacist or make a request via a web portal communicably coupled to the pharmacy computer 104A or an IVR communicably coupled or otherwise providing order data to the pharmacy computer 104A. The pharmacist determines the patient's name and accesses the pharmacy computer 104A, which receives a selection of patient information from the pharmacist via the I/O interface 128A at block 604. For example, the pharmacist accesses the pharmacy computer 104A and accesses a database of patient information, which may be stored in memory 126A or in another database either local or remote from the pharmacy computer 104A. The pharmacist can then select the name or other patient identification information in the patient information database that matches the name or other identification information of the patient 202.

At block 606, an eligibility verification request 504 is generated and/or formatted at the pharmacy computer 104A. In some example embodiments, the eligibility verification request 504 may be generated automatically by the service provider computer 106 or the claims processor computer 108, for example, as part of a standard healthcare transaction. For example, the service provider computer 106 or the claims processor computer 108 may be operable to determine that the medication/product in the healthcare transaction requires eligibility verification before processing and may generate the eligibility verification request.

In certain exemplary embodiments, the pharmacy computer 104A formats the eligibility verification request 504 with patient information (e.g., patient identifiers), Payor ID/routing information (e.g., claims processor/destination identifiers), and medication information (e.g., medication identifiers). The information can be input into the eligibility verification request 504 by the pharmacist via the I/O interface 128A or automatically retrieved and entered by the pharmacy computer 104A and, in certain situations, can be based at least in part on historical transaction information for the patient 202 in the data files 132A or a database communicably coupled to the pharmacy computer 104A. According to one example embodiment, the eligibility verification request 504 may be formatted in accordance with a version of the National Council for Prescription Drug Programs (NCPDP) Telecommunication Standard, although other standards, such as ANSI ASC X-12 Standard, Health Level 7 (HL7) Standard, or NCPDP Script Standard may be utilized as well.

The eligibility verification request 504 may include a Banking Identification Number (BIN Number), a BIN Number and Processor Control Number (PCN), or a BIN Number and Group ID for identifying a particular destination for the eligibility verification request 504. In addition, the eligibility verification request 504 may also include information relating to the patient 202, payor, prescriber, pharmacy, and/or the requested medication. As an example, the eligibility verification request 504 may include one or more of the following information:

Payor ID/Routing Information (Destination Identifier)
BIN Number, BIN Number and PCN and/or BIN Number and Group ID, that designates a destination of the eligibility verification request 504
Patient Information
Name (e.g. Patient Last Name, Patient First Name, etc.)
Date of Birth of Patient
Age of Patient
Gender of Patient
Patient Address (e.g. Street Address, City, State, Zip/Postal Code, etc.)
Patient Contact Information (e.g. Patient Telephone Number, Email Address, etc.)
Patient Health Condition Information
Patient ID or other identifier (e.g., Health Insurance Claim Number (HICN), Social Security Number, etc.)
Insurance/Coverage Information
Cardholder Name (e.g. Cardholder First Name, Cardholder Last Name)
Cardholder ID and/or other identifier (e.g. Person Code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number, Email Address, Fax Number, etc.)
Pharmacy or other Healthcare Provider Information (e.g. Store Name, Chain Identifier, etc.)
Pharmacy or other Healthcare Provider ID (e.g. NPI code)
Claim Information
Drug, service, or product information (e.g. National Drug Code (NDC) code, RxNorm code, etc.)
Prescription/Service Reference Number
Date Prescription Written
Quantity Dispensed
Days' Supply
Diagnosis/Condition (e.g., Diagnosis Code (e.g., International Statistical Classification of Diseases and Related Health Problems (ICD) Diagnosis Code)
Pricing information for the drug/service/product (e.g. Network Price, Usual & Customary price)
Number of Refills Authorized
One or more NCPDP Message Fields
One or more Drug Utilization (DUR) Codes
Date of Service.

The eligibility verification request 504 can be used to determine if the patient 202 is eligible to receive the medication identified in the request 504.

The pharmacy computer 104A can transmit the eligibility verification request 504 to the service provider computer 106 at block 608. Alternatively, the pharmacy computer 104A may transmit the eligibility verification request 504 directly to the enrollment and validation engine 112. At block 610, the service provider computer 106 receives the eligibility verification request 504. For example, the eligibility verification request 504 can be transmitted by the pharmacy computer 104A to the service provider computer 106 via the network 110. The service provider computer 106 may conduct any pre-editing, if necessary, on the eligibility verification request 504 at block 612. The pre-edits may include verifying, adding, and/or editing/correcting information included in the eligibility verification request 504 prior to it being communicated to the enrollment and validation engine 112. For example, the service provider computer 106 can parse the eligibility verification request 504 to determine/edit the financial fields, the service code, the quantity dispensed, and or the patient age.

At block 614, the medication/product identifier in the eligibility verification request 504 may be identified. For example, the service provider module 156 or another portion of the service provider computer 106 may parse the request 504 to identify the medication/product identifier (e.g., NDC code or RxNorm code) in a predetermined field of the request 504. Alternatively, enrollment and validation engine 112 may conduct the identification of the medication/product identifier in the eligibility verification request 504. At block 616, the service provider module 156 or another portion of the service provider computer 106 may compare the identified medication/product identifier to a schedule or listing of medication/product identifiers for medications/products in one or more prescription safety network programs in the REMS database 195 or another database to determine if a match exists. For example, the schedule may include the NDC code, RxNorm code or medication/product name for medications/products in a prescription safety network program that can be matched to the identified medication identifier from the eligibility verification request 504. In an alternative embodiment, the comparison may be made by the enrollment and validation engine 112.

At block 618, an inquiry is conducted to determine if the medication/product identified in the eligibility verification request 504 is in a prescription safety network program. The determination may be based on whether the comparison at block 616 identifies a match to the medication/product identifier in the eligibility verification request 504 and may be completed by the service provider module 156, another portion of the service provider computer 106, or the enrollment and validation engine 112. For example, a match would indicate that the medication/product is in a prescription safety network program. If a match is not identified based on the comparison and the medication is not in a prescription safety network program, the NO branch may be followed to block 644 of FIG. 6B. On the other hand, if a match is identified and the medication/product is in a prescription safety network program, the YES branch may be followed to block 620. In certain embodiments, if the elements of blocks 614-618 were completed by the service provider computer 106 and a match was identified, all or a portion of the data in the eligibility verification request 504 may be electronically transmitted to the enrollment and validation engine 112.

At block 620, the patient identifying information in the eligibility verification request 504 may be identified. In one example embodiment, the enrollment and validation engine 112 may parse the eligibility verification request 504 or the data therein to identify the one or more patient identifiers (e.g., patient name, date of birth, age, gender, address, contact information, HICN or social security number, etc.) in one or more predetermined fields of the request 504. At block 622, the enrollment and validation engine 112 may compare the one or more patient identifiers to a schedule or listing of patient identifiers in the REMS database 195 for patients enrolled in one or more prescription safety network programs to determine if a match exists. For example, the enrollment and validation engine 112 may use either deterministic or probabalistic matching techniques to determine if one or more of the patient identifiers from the eligibility verification request 504 match patient identifiers in one or more records of the REMS database 195.

At block 624, an inquiry is conducted to determine if the patient 202 identified in the eligibility verification request 504 is in a prescription safety network program. The determination may be based on whether the comparison at block 622 identifies a match to the one or more patient identifiers in the eligibility verification request 504 and may be completed by the enrollment and validation engine 112. For example, a match would indicate that the patient 202 is enrolled in a prescription safety network program. If a match is not identified based on the comparison and the patient 202 is not enrolled in a prescription safety network program, the NO branch may be followed to block 648 of FIG. 6B. On the other hand, if a match is identified and the patient 202 is enrolled in a prescription safety network program, the YES branch may be followed to block 626.

At block 626, the pharmacy identifier in the eligibility verification request 504 may be identified. In one example embodiment, the enrollment and validation engine 112 may parse the eligibility verification request 504 or the data therein to identify the pharmacy identifier (e.g., NPI code, store name, chain identifier, or pharmacist name) in one or more predetermined fields of the request 504. At block 628, the enrollment and validation engine 112 may compare the pharmacy identifier to a schedule or listing of pharmacy identifiers in the REMS database 195 for pharmacies/pharmacists enrolled in one or more prescription safety network programs to determine if a match exists.

At block 630, an inquiry is conducted to determine if the pharmacy/pharmacist identified in the eligibility verification request 504 is in a prescription safety network program. The determination may be based on whether the comparison at block 628 identifies a match to the pharmacy identifier in the eligibility verification request 504 and may be completed by the enrollment and validation engine 112. For example, a match would indicate that the pharmacy/pharmacist 206 is enrolled in a prescription safety network program. If a match is not identified based on the comparison and the pharmacy/pharmacist 206 is not enrolled in a prescription safety network program, the NO branch may be followed to block 648 of FIG. 6B. Otherwise, if a match is identified and the pharmacy/pharmacist 206 is enrolled in a prescription safety network program, the YES branch may be followed to block 632.

In an alternate embodiment, if a match is not identified, the pharmacy/pharmacist may be determined to be not enrolled and a request to enroll along with any associated enrollment information and prescription safety network program requirements may be identified and transmitted to the pharmacy computer 104A. The pharmacy/pharmacist may then enroll in the prescription safety network program by filling out and sending back the enrollment information, including the pharmacy/pharmacist identification data to the enrollment and validation engine 112 (e.g., via the service provider computer 106) and satisfying the other requirements of the prescription safety network program. Upon proper enrollment, the pharmacy/pharmacist identification data may be stored in the REMS database 195, the pharmacy/pharmacist may be considered enrolled in a prescription safety network program, and the YES branch may be followed to block 632

At block 632, the prescriber identifier in the eligibility verification request 504 may be identified. In one example embodiment, the enrollment and validation engine 112 may parse the eligibility verification request 504 or the data therein to identify the prescriber identifier (e.g., DEA number) in a predetermined field of the request 504. At block 634, the enrollment and validation engine 112 may compare the prescriber identifier to a schedule or listing of prescriber identifiers in the REMS database 195 for prescribers who have been deactivated or otherwise stripped of enrollment rights in the prescription safety network program to determine if a match exists. For example, when it is determined that a physician or other prescriber is failing to satisfy the requirements of the prescription safety network program (e.g., for abuse, diversion, or the like), the prescriber's enrollment information in the physician REMS database 194 may be flagged to designate that the prescriber's rights as an enrolled prescriber in the prescription safety network program have been removed. Further, when this occurs, the prescriber identifier for that prescriber may be added to a table, listing, or schedule of deactivated prescribers in the REMS database 195.

At block 636, an inquiry is conducted to determine if the prescriber identified in the eligibility verification request 504 is a deactivated prescriber in the prescription safety network program. The determination may be based on whether the comparison at block 634 identifies a match to the prescriber identifier in the eligibility verification request 504 and may be completed by the enrollment and validation engine 112. For example, a match would indicate that the prescriber 204 has been deactivated or otherwise expelled from a prescription safety network program. If a match is identified based on the comparison and the prescriber 204 has been deactivated from a prescription safety network program, the YES branch may be followed to block 648 of FIG. 6B. Otherwise, if a match is not identified and the prescriber 206 is presumed to be enrolled in a prescription safety network program (based on the enrollment of the patient 202), the NO branch may be followed to block 638.

At block 638, the service provider computer 106 may use the medication/product identifiers and the one or more patient identifiers in the eligibility verification request 504 for comparison against historical healthcare transactions in the historical claims database 196 to identify one or more matching records for prior healthcare transactions for the patient 202 in the particular prescription safety network program. At block 640, the service provider computer 106 may compare the prescriber identifier in the eligibility verification request 504 to the prescriber identifiers in the one or more matching records for prior healthcare transactions for the patient 202 in the historical claims database 196. In one example, embodiment, the comparison may be made only to the most recent prior healthcare transaction for the patient 202 and medication/product identified in the request 504. In certain example embodiments, comparison to prior healthcare transactions for the patient 202 may be conducted to determine if the current prescriber is different from the previous prescriber that prescribed the medication/product to the patient 202. A difference in prescribers may indicate that the patient 202 is going to multiple doctors to obtain the same medication (e.g., doctor shopping). Further, since, in certain example embodiments, the prescriber enrollment in a prescription safety network program is not evaluated but is instead assumed based on the fact that the prescriber enrolls the patient 202 and the patient 202 being enrolled raises a presumption that the prescriber is enrolled, a change in prescribers for the patient 202 for the particular medication under the prescription safety network program raises the possibility that the prescriber is not enrolled in the prescription safety network program.

At block 642, an inquiry is conducted to determine if the prescriber identifier in the eligibility verification request 504 matches the prescriber identifier in one or more prior healthcare transactions for the patient 202 in the historical claims database 196. The determination may be based on whether the comparison at block 640 identifies a match to the prescriber identifier in the eligibility verification request 504 and may be completed by the service provider computer 106. If a match is identified based on the comparison, the YES branch may be followed to block 644 of FIG. 6B. Otherwise, if a match is not identified, the NO branch may be followed to block 648 of FIG. 6B.

In certain example embodiments, additional evaluations and comparisons may be conducted. For example, the enrollment and validation engine 112 may identify the refill number for the particular eligibility verification request 504. The enrollment and validation engine 112 may compare the refill number to a threshold refill level for the particular medication/product or prescription safety network program. In one example embodiment, the threshold refill level may represent the maximum number of refills that the patient 202 may receive under the prescription safety network program before the patient 202 has to go back to the prescriber and be re-enrolled into the program. If the refill number equals the threshold refill level for the particular program, the enrollment and validation engine 112 may consider the patient 202 enrolled for the current transaction but may also deactivate or otherwise delete the patient's enrollment identification data from the REMS database 195 for the particular prescription safety network program.

In another alternate embodiment, a multi-step verification process may be completed to determine that the patient 202, pharmacy, and prescriber are enrolled in the prescription safety network program for the medication identified in the eligibility verification request 504. First the patient 202 and pharmacy identified in the request 504 can be evaluated to determine if each is enrolled in the prescription safety network program by querying the REMS database 195. Once the patient 202 and pharmacy/pharmacist are determined to be enrolled in the manner described in blocks 620-630, a wholly-separate verification may be conducted to determine if the prescriber is enrolled in the prescription safety network program by separately querying the physician REMS database 194. The enrollment and validation engine 112 may compare the prescriber identifier (e.g., DEA number) in the eligibility verification request 504 to the stored prescriber identifiers for enrolled prescribers in a particular prescription safety network program in the physician REMS database 194. If a match is identified, the prescriber may be determined to be enrolled in the prescription safety network program and the process may continue to block 644.

At block 644, an approval response 506 to the eligibility verification request 504 signifying that the requirements for a prescription safety network program associated with the medication/product identified in the request 504 have been satisfied may be generated. In one example embodiment, the approval response 506 may be generated by the enrollment and validation engine 112 and forwarded to the service provider computer 106. Alternatively, the enrollment and validation engine 112 may signal the service provider computer 106 that the requirements for the prescription safety network have been satisfied and the service provider module 156 or another portion of the service provider computer 106 may generate the approval response 506. In one example embodiment, the approval response 506 may be a code or text inserted into a predetermined field of the eligibility verification request 504. At block 646, the service provider computer 106 may electronically transmit the approval response 506 via the network 110 to the pharmacy computer 104A from which the request 504 originated. The process may then continue to block 652.

In block 648, a rejection response 508 to the eligibility verification request 504 signifying that the requirements for a prescription safety network program associated with the medication/product identified in the request 504 have not been satisfied may be generated. In one example embodiment, the rejection response 508 may be generated by the enrollment and validation engine 112 and forwarded to the service provider computer 106. Alternatively, the enrollment and validation engine 112 may signal the service provider computer 106 that the requirements for the prescription safety network have not been satisfied and the service provider module 156 or another portion of the service provider computer 106 may generate the rejection response 508. In one example embodiment, the rejection response 508 may be a code or text inserted into a predetermined field of the eligibility verification request 504. At block 648, the service provider computer 106 may electronically transmit the rejection response 508 via the network 110 to the pharmacy computer 104A from which the request 504 originated. The process may then continue to block 652.

At block 652, all or a portion of the data from the request 504 and the response 506 or 508 may be stored in a database. For example, the service provider computer 106 may store the data from the request 504 and the response 506 or 508 in the historical claims database 196. At block 654, the pharmacy computer 104A receives the response 506 or 508 to the request 504. In certain example embodiments, if the response is an approval response 506, the pharmacist may then generate and send a second healthcare transaction, (e.g., a prescription claim transaction) to determine coverage and co-pay requirements for the patient 202.

For example, at block 656, a prescription claim transaction 510 is generated and/or formatted at the pharmacy computer 104A. In certain exemplary embodiments, the pharmacy computer 104A formats the prescription claim transaction 510 with patient information (e.g., patient identifiers), Payor ID/routing information (e.g., claims processor/destination identifiers), and medication information (e.g., medication identifiers). The information can be input into the prescription claim transaction 510 by the pharmacist via the I/O interface 128A or automatically retrieved and entered by the pharmacy computer 104A and, in certain situations, can be based at least in part on historical transaction information for the patient 202 in the data files 132A or a database communicably coupled to the pharmacy computer 104A. According to one example embodiment, the prescription claim transaction 510 may be formatted in accordance with a version of the National Council for Prescription Drug Programs (NCPDP) Telecommunication Standard, although other standards, such as ANSI ASC X-12 Standard, Health Level 7 (HL7) Standard, or NCPDP Script Standard may be utilized as well.

The prescription claim transaction 510 may include a BIN Number, a BIN Number and PCN, or a BIN Number and Group ID for identifying a particular claims processor computer (e.g., ACO, PBM, payor, healthcare insurance company, Medicare or other government healthcare insurance payor, Medicare Part D provider, etc.), such as the claims processor computer 108, as a destination for the prescription claim transaction 510. In addition, the prescription claim transaction 510 may also include information relating to the patient, payor, prescriber, healthcare provider, and/or the requested medication. As an example, the prescription claim transaction 510 may include one or more of the following information:

Payor ID/Routing Information (Destination Identifier)
BIN Number, BIN Number and PCN and/or BIN Number and Group ID, that designates a destination of the prescription claim transaction 302
Patient Information
Name (e.g. Patient Last Name, Patient First Name, etc.)
Date of Birth of Patient
Age of Patient
Gender of Patient
Patient Address (e.g. Street Address, City, State, Zip/Postal Code, etc.)
Patient Contact Information (e.g. Patient Telephone Number, Email Address, etc.)
Patient Health Condition Information
Patient ID or other identifier (e.g., Health Insurance Claim Number (HICN), Social Security Number, etc.)
Insurance/Coverage Information
Cardholder Name (e.g. Cardholder First Name, Cardholder Last Name)
Cardholder ID and/or other identifier (e.g. Person Code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number, Email Address, Fax Number, etc.)
Pharmacy or other Healthcare Provider Information (e.g. Store Name, Chain Identifier, etc.)
Pharmacy or other Healthcare Provider ID (e.g. NPI code)
Claim Information
Drug, service, or product information (e.g. National Drug Code (NDC) code, RxNorm code, etc.)
Prescription/Service Reference Number
Date Prescription Written
Quantity Dispensed
Days' Supply
Diagnosis/Condition (e.g., Diagnosis Code (e.g., International Statistical Classification of Diseases and Related Health Problems (ICD) Diagnosis Code)
Pricing information for the drug/service/product (e.g. Network Price, Usual & Customary price)
Number of Refills Authorized
One or more NCPDP Message Fields
One or more Drug Utilization (DUR) Codes
Date of Service.

The prescription claim transaction 510 can be used to determine if the claims processor associated with the claims processor computer 108 approves or rejects payment coverage for medication being requested in the prescription claim transaction 510 and, if approved, the amount the claims processor will cover (or pay) for the medication being requested and how much the patient co-pay amount will be.

The pharmacy computer 104A can transmit the prescription claim transaction 510 to the service provider computer 106 at block 658. At block 660, the service provider computer 106 receives the prescription claim transaction 510. For example, the prescription claim transaction 510 can be transmitted by the pharmacy computer 104A to the service provider computer 106 via the network 110. The service provider computer 106 may conduct any pre-editing, if necessary, on the prescription claim transaction 510 at block 662. The pre-edits may include verifying, adding, and/or editing information included in the prescription claim transaction 510 prior to it being communicated to a claims processor computer 108.

At block 664, the service provider computer 106 may transmit the prescription claim transaction 510 to the claims processor computer 108 associated with the destination identifier in the transaction 510. At block 666, the claims processor computer 108 can receive the prescription claim transaction 510 from the service provider computer 106, and can adjudicate or otherwise process the prescription claim transaction 510. For example, the claims processor computer 108 may determine benefits coverage for the prescription claim transaction 510 according to an adjudication process associated with eligibility, pricing, and/or utilization review. At block 668, the claims processor computer 108 may transmit or otherwise communicate an adjudicated response 512 of the prescription claim transaction 510 to the service provider computer 106 via, for example, the network 110. The adjudicated response 512 may include, without limitation, a transaction status indicator indicating whether the prescription claim transaction 510 was paid or rejected. In one example embodiment, when the prescription claim transaction 510 is paid, the adjudicated response 512 may include a transaction status indicator "P". If, however, the prescription claim transaction 510 is rejected, the adjudicated response 512 may include a transaction indicator "R".

In one example, when the adjudicated response 512 includes a transaction status indicator "P", the adjudicated response 512 may also include, without limitation, one or more fields comprising a patient pay amount field (the patient co-pay) populated with a value returned by the claims processor computer 108, an associated quantity dispensed field populated with a submitted quantity to be dispensed on the prescription claim transaction 510, and/or a pharmacy name field populated with a short pharmacy name corresponding to the submitted pharmacy identifier on the prescription claim transaction 510.

If, on the other hand, the adjudicated response 512 includes the transaction status indicator "R", the adjudicated response 512 may also include, without limitation, one or more fields comprising the patient pay amount field left blank, the associated dispensed quantity field left blank, a reject reason field populated with a reject code (e.g., pricing not available for an identified scenario, reject description, patient not covered, medication not in formulary, or the like), the pharmacy name field is left blank, a reason for service code field populated with a reject error code, and/or a reason for service description field populated with an abbreviated description of the corresponding reason for service code.

At block 670, the service provider computer 106 receives the adjudicated response 512 from the claims processor computer 108. Upon receipt, the service provider computer 106 may determine whether the prescription claim transaction 510 was approved for payment or denied/rejected by the claims processor computer 108. In one example, the service provider computer 104 may parse the adjudicated response 512 to identify the transaction status indicator in the response 512. The service provider computer 106 may also store the all or a portion of the data (e.g., the one or more patient identifiers, the medication/product identifier, the pharmacy identifier, the prescriber identifier, and the adjudication) from the prescription claim transaction 510 and adjudicated response 512 in the historical claims database 196.

The service provider computer 106 may transmit or otherwise communicate the adjudicated response 512 to the pharmacy computer 104A via, for example, the network 110 at block 672. At block 674, the pharmacy computer 104A can receive the adjudicated response 512. If the adjudicated response 512 is approved/paid, the pharmacy associated with the pharmacy computer 104A may dispense the requested medication, product, or service identified in the prescription claim transaction 510 to the patient 202 at block 676. If the adjudicated response 512 is a denial/rejection of the prescription claim transaction 510, then the pharmacy/pharmacist can inform the patient 202 of the reason for the denial/rejection based on the reject code included in the adjudicated response 512. The process may continue to the END block.

In certain embodiments, in addition to the method described above, each time the patient 202 fills the prescription and the pharmacist dispenses the medication/product to the patient 202, the enrollment and validation engine 112 and/or the service provider computer, based on an evaluation of the adjudicated response 512 may generate and electronically transmit a message to the prescriber identified in the prescription claim transaction 510 notifying the prescriber that the prescription has been filled.

In certain alternate embodiments, rather than two separate healthcare transactions being submitted by the pharmacy/pharmacist via the pharmacy computer 104A, a single healthcare transaction may be submitted. In this alternate embodiment, rather than transmitting an approval response to the pharmacy computer 104A once the determination is made that the requirements for the prescription safety network have been satisfied, the healthcare transaction may be electronically transmitted to the claims processor computer 108 for adjudication in substantially the same manner as described in block 664. The healthcare transaction may then be adjudicated by the claims processor computer and transmitted back the pharmacy computer 104A via the service provider computer 106 in substantially the manner described in blocks 666-676.

The methods described and shown in FIGS. 2-6B may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 2-6B may be performed. Likewise, while FIGS. 3, 4, and 6A-B have been described primarily in conjunction with FIGS. 2 and 5 it will be appreciated that variations of FIGS. 2 and 5 are available. In addition, in certain embodiments, the portions of the methods described in FIGS. 2-6B may be completed by different entities. For example, in certain embodiments the enrollment process into the prescription safety network programs, described with reference to FIGS. 2-4, may be completed by a first entity, and the healthcare transaction evaluation, described with reference to FIGS. 5-6B, to determine if the requirements for the prescription safety network program have been satisfied (e.g., the patient and pharmacy/pharmacist identified in the healthcare transaction are enrolled in the prescription safety network program covering the prescribed medication/product) and the mediation/product can be dispensed to the patient may be completed by a second entity separate and wholly unrelated to the first entity. In other embodiments, the evaluation of the healthcare transaction to determine if the pharmacy and patient are enrolled in the prescription safety network program may be completed by a first entity while a comparison of the medication identifier, one or more patient identifiers, and prescriber identifier in the healthcare transaction to historical claim data to determine if potential abuse or diversion is occurring may be completed by a second entity separate and wholly unrelated to the first entity.

Accordingly, example embodiments disclosed herein can provide the technical effects of creating a system and methods that provide a real-time or near real time way to enroll in a prescription safety network program and determine if the requirements for a prescription safety network program have been satisfied as part of the processing of a healthcare transaction. In this regard, patients, prescribers, pharmacies and wholesale distributors are more likely to have satisfied the requirements of the prescription safety network program and the patients are more likely to be properly educated as set forth in the particular prescription safety network program before the patient 202 would be able to receive and the pharmacy would be able to dispense the medication/product under that prescription safety network program.

Further, example embodiments disclosed herein can provide the technical effects of creating a system and methods that provide for the enrollment of prescribers in one or more prescription safety network programs and the storage of the prescriber enrollment information in a first database. The system and methods may also provide for the enrollment of patients and pharmacies/pharmacists in the one or more prescription safety network programs and the storage of the patient enrollment information and the pharmacy/pharmacist enrollment information in a second database separate and distinct from the first database such that prescriber enrollment data in the first database is not accessible to a query directed to the second database. Thus, the prescriber enrollment data may be kept confidential from patients and/or pharmacies/pharmacists enrolling in a prescription safety network program and from queries to determine if the patients or pharmacies/pharmacists are enrolled in the prescription safety network program.

Still further, example embodiments disclosed herein can provide the technical effects of creating a system and methods that provide a single physician REMS database 194 for enrolling prescribers in multiple prescription safety network programs. As such, a prescriber only has to enroll and provide physician enrollment information once to the physician REMS database 194. The prescriber may then simply confirm satisfaction of the education or other requirements for each additional prescription safety network program that the prescriber enrolls in and may be provided with unique log-in access for each particular prescription safety network program.

While certain example embodiments disclosed herein describe the enrollment and validation engine 112 as being separate of the service provider computer 106, in alternate embodiments, the enrollment and validation engine 112 or the functions that it completes may be part of the service provider computer 106. In those embodiments where the enrollment and validation engine 112 is incorporated into the service provider computer 106, and with regard to the methods described above, the blocks describing transmitting or receiving between the service provider computer 106 and the enrollment and validation engine 112 may be internal transmissions within the service provider computer 106 or may be omitted altogether. Further, while the exemplary embodiments described herein disclose certain actions occurring at the service provider computer 106 and/or the enrollment and validation engine 112, in alternative embodiments those actions described with reference to FIGS. 1-6B may alternately be completed at a pharmacy computer 104A, a prescriber computer 104B, an enrollment and validation engine 112, a separate physician enrollment and validation engine (not shown) any combination thereof, and/or a combination of those devices along with the service provider computer 106. In those alternate embodiments, certain transmission/receiving actions described above with reference to FIGS. 1-6B may be omitted while others may be added, as understood by one or ordinary skill in the art. The intent being that in alternate embodiments, any of the devices/computers discussed in FIG. 1 are capable of completing any or any part of the methods described with reference to FIGS. 2-6B.

Various block and/or flow diagrams of systems and methods and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the disclosure may provide for a computer program product, that includes a computer usable medium (e.g., transitory or non-transitory) having a computer-readable program code or program instructions embodied therein, said computer-readable program code adapted to be executed to implement one or more functions specified in the flow diagram step or steps. The computer program instructions may also be loaded onto a computer or other programmable data processing apparatus to cause a series of operational elements or actions to be performed on the computer or other programmable apparatus to produce a computer-implemented process such that the instructions that execute on the computer or other programmable apparatus provide elements or steps for implementing the functions specified in the flow diagram blocks.

Accordingly, blocks of the block diagrams and flow diagrams support combinations of means for performing the specified functions, combinations of elements or actions for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of those set forth herein will be apparent having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system comprising:
   at least one memory operable to store computer-executable instructions;
   a first database configured to receive and store a plurality of prescriber enrollment data associated with a plurality of prescribers for one or more prescription safety network programs;
   a second database configured to receive and store a plurality of patient enrollment data associated with a plurality of patients for the one or more prescription safety network programs;
   a third database configured to receive and store a plurality of pharmacist enrollment data for a plurality of pharmacists for the one or more prescription safety network programs; and
   at least one processor configured to access the at least one memory and execute the computer-executable instructions to:
      receive prescriber enrollment data for enrollment of a prescriber in a prescription safety network program;
      store the prescriber enrollment data in the first database;
      direct communication of an enrollment right to the prescriber for enrolling one or more patients in the prescription safety network program in response to receiving the prescriber enrollment data;
      receive, from the prescriber, patient enrollment data for enrolling a patient in the prescription safety network program, wherein the patent enrollment data comprises a patient identifier;

store the patient enrollment data and the patient identifier in the second database, wherein the second database comprises a plurality of database records each comprising patient enrollment data and a patient identifier for a respective patient;

receive, from a distributor of a first medication, pharmacist enrollment data for enrolling a first pharmacist in the prescription safety network program for the first medication, wherein the pharmacist enrollment data is indicative of the distributor having provided the first pharmacist with dispensing rights for the first medication;

receive from a pharmacy computer associated with the first pharmacist, a healthcare transaction comprising a medication identifier associated with the first medication and the patient identifier associated with the patient;

determine, without accessing the first database or the third database, that the patient identifier is associated with a database record of the plurality of database records in the second database, wherein the database record associated with the patient comprises the patient identifier of the patient enrollment data received from the prescriber;

determine, based on the database record associated with the patient and the pharmacist enrollment data being indicative of the distributor having provided the first pharmacist with dispensing rights for the first medication, that the patient is enrolled in the prescription safety network program and the first pharmacist has dispensing rights for the first medication; and generate, without accessing the first database or the third database, an approval response to the healthcare transaction based on the determination that the patient is enrolled in the prescription safety network program and the first pharmacist has dispensing rights for the first medication.

2. The system of claim 1, wherein the received healthcare transaction further comprises a pharmacy identifier identifying a pharmacy, and wherein the at least one processor is further configured to access the at least one memory and execute the computer-executable instructions to:

receive pharmacist enrollment data for enrolling a pharmacist in the prescription safety network program; and store the pharmacist enrollment data in the third database.

3. The system of claim 2, wherein the at least one processor is further configured to access the at least one memory and execute the computer-executable instructions to:

determine, based on the pharmacy identifier and the pharmacist enrollment data in the third database, that the pharmacy identifier matches the pharmacist enrollment data;

wherein the approval response to the healthcare transaction is generated based on a positive determination that the at least one patient identifier matches the patient enrollment data and the pharmacy identifier matches the pharmacist enrollment data.

4. The system of claim 1, wherein the second database is further configured to receive and store a plurality of deactivated prescriber identifiers for a plurality of prescribers, wherein each of the plurality of prescribers has had the respective enrollment right removed from the respective prescriber for the one or more prescription safety network programs, wherein the received healthcare transaction further comprises a prescriber identifier identifying a prescriber of the medication to the patient, and wherein the at least one processor is further configured to access the at least one memory and execute the computer-executable instructions to:

receive the plurality of prescriber identifiers;

store the plurality of prescriber identifiers in the second database;

identify the prescriber identifier in the healthcare transaction;

determine, based on the prescriber identifier and the plurality of deactivated prescriber identifiers in the second database, that the prescriber identifier matches at least one of the plurality of deactivated prescriber identifiers; and wherein the approval response to the healthcare transaction is generated based on a positive determination that the at least one patient identifier matches the patient enrollment data and the prescriber identifier does not match any of the plurality of deactivated prescriber identifiers.

5. The system of claim 1, wherein the at least one processor is configured to determine, based on an evaluation of the medication identifier, that the medication is in the prescription safety network program by accessing the at least one memory and executing the computer-executable instructions to:

identify the medication identifier in the healthcare transaction;

identify a plurality of medication identifiers in the prescription safety network program; and determine, based on the medication identifier in the healthcare transaction and the plurality of medication identifiers in the prescription safety network program, that the medication identifier in the healthcare transaction matches at least one of the plurality of medication identifiers in the prescription safety network program;

wherein the medication is determined to be in the prescription safety network program based on a positive determination that the medication identifier in the healthcare transaction matches at least one of the plurality of medication identifiers in the prescription safety network program.

6. The system of claim 1, wherein the at least one processor is further configured to access the at least one memory and execute the computer-executable instructions to direct communication of the enrollment right to the prescriber in the form of log-in credentials, wherein the log-in credentials are required to enroll a patient in the prescription safety network program.

7. The system of claim 1, wherein the at least one processor is further configured to access the at least one memory and execute the computer-executable instructions to:

determine, based on at least one of the medication identifier or an identity of the prescription safety network program, educational information for review by the prescriber;

retrieve the determined educational information;

direct communication of the educational information to the prescriber; and receive, from the prescriber, a confirmation of understanding of the educational information;

wherein the prescriber enrollment data is stored in the first database in response to the receipt of the confirmation of understanding of the educational information.

8. The system of claim 1, wherein the at least one processor is further configured to access the at least one memory and execute the computer-executable instructions to:
- determine, based on at least one of the medication identifier and an identity of the prescription safety network program, at least one certification needed by the prescriber to enroll in the prescription safety network program;
- retrieve a certification information for the determined certification needed by the prescriber;
- direct communication of the certification information to the prescriber; and receive, from the prescriber, a confirmation of receipt of the certification by the prescriber;
- wherein the prescriber enrollment data is stored in the first database in response to the receipt of the confirmation of receipt of the certification by the prescriber.

9. The system of claim 1, wherein the at least one processor is further configured to access the at least one memory and execute the computer-executable instructions to:
- receive a log-in request from a prescriber computer for the prescriber;
- generate a patient enrollment form in response to the received log-in request; and direct communication of the patient enrollment form to the prescriber.

10. A computer-implemented method, comprising:
- receiving, by one or more service provider computers associated with a service provider and comprising one or more processors from a prescriber computer associated with a prescriber of medication, prescriber enrollment data for a prescription safety network program, wherein the prescriber enrollment data comprises a prescriber identifier for the prescriber;
- storing, by the one or more service provider computers, the prescriber enrollment data in a first database comprising a plurality of prescriber enrollee information for the prescription safety network program;
- providing, by the one or more service provider computers to the prescriber, enrollment rights in a second database for a plurality of patients in response to receiving the prescriber enrollment data for the prescription safety network program;
- receiving, by the one or more service provider computers from the prescriber computer, patient enrollment data for enrolling a patient in the prescription safety network program, wherein the patient enrollment data comprises a patient associated with a patient;
- storing, by the one or more service provider computers, the patient enrollment data and the patient identifier in the second database, wherein the second database comprises a plurality of database records each comprising patient enrollment data and a patient identifier for a respective patient enrolled in the prescription safety network program;
- receiving, by the one or more service provider computers, from a distributor of a first medication, pharmacist enrollment data for enrolling a first pharmacist in the prescription safety network program for the first medication, wherein the pharmacist enrollment data is indicative of the distributor having provided the first pharmacist with dispensing rights for the first medication
- receiving, by the one or more service provider computers, a healthcare transaction comprising a medication identifier associated with the first medication and the patient identifier associated with the patient;
- determining, by the one or more service provider computers, without accessing the first database, that the patient identifier is associated with a database record of the plurality of database records in the second database, wherein the database record associated with the patient comprises the identifier of the patient enrollment data received from the prescriber computer;
- determine, based on the database record associated with the patient and the pharmacist enrollment data being indicative of the distributor having provided the first pharmacist with dispensing rights for the first medication, that the patient is enrolled in the prescription safety network program and the first pharmacist has dispensing rights for the first medication; and
- generating, without accessing the first database, by the one or more service provider computers, an approval response to the healthcare transaction based on the determination that the patient is enrolled in the prescription safety network program and the first pharmacist has dispensing rights for the first medication.

11. The computer-implemented method of claim 10, wherein the received healthcare transaction further comprises a pharmacy identifier identifying a pharmacy, and wherein the method further comprises:
- receiving, by the one or more service provider computers from a pharmacy computer associated with the pharmacy, pharmacist enrollment data for the prescription safety network program, wherein the pharmacist enrollment data comprises a pharmacist identifier for a pharmacist at the pharmacy; and
- storing, by the one or more service provider computers, the pharmacist enrollment data in a third database comprising a plurality of pharmacy enrollee information for the prescription safety network program.

12. The computer-implemented method of claim 11, further comprising:
- determining, by the one or more service provider computers and based on the pharmacy identifier and the plurality of pharmacy enrollee information in the third database, that the pharmacy identifier matches at least one of the plurality of pharmacy enrollee information;
- wherein the approval response to the healthcare transaction is generated based on a positive determination that the at least one patient identifier matches at least one of the plurality of patient enrollee information and the pharmacy identifier matches at least one of the plurality of pharmacy enrollee information.

13. The computer-implemented method of claim 10, wherein the received healthcare transaction further comprises a prescriber identifier identifying a pharmacy, and wherein the method further comprises:
- receiving, by the one or more service provider computers, a plurality of deactivated prescriber identifiers for a plurality of prescribers, wherein each of the plurality of prescribers has had the respective enrollment right removed from the respective prescriber for the one or more prescription safety network programs; and
- storing, by the one or more service provider computers, the plurality of deactivated prescriber identifiers in the second database;
- identifying, by the one or more service provider computers, the prescriber identifier in the healthcare transaction;
- determining, by the one or more service provider computers and based on the prescriber identifier and the plurality of deactivated prescriber identifiers in the second database, that the prescriber identifier matches at least one of the plurality of deactivated prescriber identifiers; and wherein the approval response to the healthcare transaction is generated based on a positive determination that the at least one patient identifier matches the patient enrollment data and the prescriber identifier does not match any of the plurality of deactivated prescriber identifiers.

14. The computer-implemented method of claim 10, wherein determining, based on an evaluation of the medication identifier, that the medication is in the prescription safety network program comprises:

identifying, by the one or more service provider computers, the medication identifier in the healthcare transaction;

identifying, by the one or more service provider computers, a plurality of medication identifiers in the prescription safety network program; and determining, by the one or more service provider computers and based on the medication identifier in the healthcare transaction and the plurality of medication identifiers in the prescription safety network program, that the medication identifier in the healthcare transaction matches at least one of the plurality of medication identifiers in the prescription safety network program;

wherein the medication is determined to be in the prescription safety network program based on a positive determination that the medication identifier in the healthcare transaction matches at least one of the plurality of medication identifiers in the prescription safety network program.

15. The computer-implemented method of claim 10, further comprising transmitting the enrollment right to the prescriber in the form of log-in credentials, wherein the log-in credentials are required to enroll a patient in the prescription safety network program.

16. The computer-implemented method of claim 10, further comprising:

determining, by the one or more service provider computers and based on at least one of the medication identifier or an identity of the prescription safety network program, educational information for review by the prescriber;

retrieving, by the one or more service provider computers, the determined educational information;

transmitting, by the one or more service provider computers, the educational information to the prescriber; and receiving, by the one or more service provider computers and from the prescriber, a confirmation of understanding of the educational information;

wherein the prescriber enrollment data is stored in the first database in response to the receipt of the confirmation of understanding of the educational information.

17. The computer-implemented method of claim 10, further comprising:

determining, by the one or more service provider computers and based on at least one of the medication identifier or an identity of the prescription safety network program, at least one certification needed by the prescriber to enroll in the prescription safety network program;

retrieving, by the one or more service provider computers, a certification information for the determined certification needed by the prescriber;

transmitting, by the one or more service provider computers, the certification information to the prescriber; and receiving, by the one or more service provider computers and from the prescriber, a confirmation of receipt of the certification by the prescriber, wherein the prescriber enrollment data is stored in the first database in response to the receipt of the confirmation of receipt of the certification by the prescriber.

18. The computer-implemented method of claim 10, further comprising:

receiving, by the one or more service provider computers, a log-in request from a prescriber computer for the prescriber;

generating, by the one or more service provider computers, a patient enrollment form in response to the received log-in request; and transmitting, by the one or more service provider computers, the patient enrollment form to the prescriber.

* * * * *